US009974859B2

(12) United States Patent
Karp et al.

(10) Patent No.: US 9,974,859 B2
(45) Date of Patent: May 22, 2018

(54) NANOSTRUCTURED GELS CAPABLE OF CONTROLLED RELEASE OF ENTRAPPED AGENTS

(71) Applicants: The Brigham and Women's Hospital, Inc., Boston, MA (US); Massachusetts Institute of Technology, Cambridge, MA (US)

(72) Inventors: Jeffrey M. Karp, Brookline, MA (US); Praveen Kumar Vemula, Cambridge, MA (US); Nathaniel R. Campbell, Baltimore, MD (US); Abdullah M. Syed, Mississauga (CA); Sufeng Zhang, Cambridge, MA (US); Omid C. Farokhzad, Waban, MA (US); Robert S. Langer, Newton, MA (US)

(73) Assignees: The Brigham and Women's Hospital, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 0 days. days.

(21) Appl. No.: 15/174,267

(22) Filed: Jun. 6, 2016

(65) Prior Publication Data
US 2017/0000888 A1 Jan. 5, 2017

Related U.S. Application Data

(63) Continuation of application No. 13/825,486, filed as application No. PCT/US2011/053075 on Sep. 23, 2011, now abandoned.

(60) Provisional application No. 61/386,268, filed on Sep. 24, 2010, provisional application No. 61/466,753, filed on Mar. 23, 2011.

(51) Int. Cl.
*A61K 47/22* (2006.01)
*A61K 38/28* (2006.01)
*A61K 31/4188* (2006.01)
*A61K 31/405* (2006.01)
*A61K 31/713* (2006.01)
*A61K 31/4745* (2006.01)
*A61K 31/58* (2006.01)
*A61K 9/107* (2006.01)
*A61K 47/14* (2017.01)
*A61K 9/06* (2006.01)
*A61K 47/26* (2006.01)
*A61K 31/573* (2006.01)
*A61K 47/28* (2006.01)
*A61K 9/00* (2006.01)
*A61K 31/166* (2006.01)

(52) U.S. Cl.
CPC ............ *A61K 47/22* (2013.01); *A61K 9/0019* (2013.01); *A61K 9/06* (2013.01); *A61K 9/1075* (2013.01); *A61K 31/166* (2013.01); *A61K 31/405* (2013.01); *A61K 31/4188* (2013.01); *A61K 31/4745* (2013.01); *A61K 31/573* (2013.01); *A61K 31/58* (2013.01); *A61K 31/713* (2013.01); *A61K 38/28* (2013.01); *A61K 47/14* (2013.01); *A61K 47/26* (2013.01); *A61K 47/28* (2013.01)

(58) Field of Classification Search
None
See application file for complete search history.

(56) References Cited

U.S. PATENT DOCUMENTS

| | | | |
|---|---|---|---|
| 5,603,959 A | 2/1997 | Horrobin | |
| 6,471,970 B1 | 10/2002 | Fanara | |
| 7,749,485 B2 | 7/2010 | Tournier | |
| 2005/0084470 A1* | 4/2005 | Abbas | A61K 8/97 424/70.22 |
| 2006/0276676 A1 | 12/2006 | van Bommel et al. | |
| 2008/0004398 A1 | 1/2008 | Durrieu | |
| 2008/0038316 A1* | 2/2008 | Wong | A61K 9/0024 424/426 |
| 2009/0110735 A1* | 4/2009 | Maggio | A61K 9/0014 424/488 |
| 2009/0169498 A1 | 7/2009 | de Jong | |
| 2009/0257968 A1* | 10/2009 | Walton | A61K 8/042 424/64 |
| 2010/0129451 A1 | 5/2010 | John et al. | |
| 2013/0273140 A1 | 10/2013 | Maggio | |
| 2013/0280334 A1 | 10/2013 | Karp | |
| 2013/0309286 A1* | 11/2013 | Engstad | A61K 9/0014 424/402 |
| 2014/0302144 A1 | 10/2014 | Koutsopoulos | |
| 2015/0202586 A1 | 7/2015 | Imoto | |

FOREIGN PATENT DOCUMENTS

| | | | |
|---|---|---|---|
| EP | 1063007 A1 * | 12/2000 | ........... A61K 8/0212 |
| EP | 0517211 | 9/2004 | |
| EP | 2361640 | 8/2011 | |

(Continued)

OTHER PUBLICATIONS

EP 1063007 A1 original and machine translation.*
Szüts et al., "Study of thermo-sensitive gel-forming properties of sucrose stearates", J Excipients and Food Chem 1(2): 13-20 (2010).*
J Excipients Food Chem vol. 1 No. 2 2010—publication date.*
Ullrich et al., "Sucrose ester nanodispersions: Microviscosity and viscoelastic properties", Eur J Pharmaceutics Biopharmaceutics 70: 550-555 (2008).*
van Esch et al., "New functional materials based on self-assembling organogels: From serendipity towards design", Angew Chem Int Ed 39: 2263-2266 (2000).*

(Continued)

*Primary Examiner* — Robert A Wax
*Assistant Examiner* — Thor Nielsen
(74) *Attorney, Agent, or Firm* — Pabst Patent Group LLP

(57) ABSTRACT

Self-assembled gel compositions including a gelator, e.g., an enzyme-cleavable gelator, e.g., having a molecular weight of 2500 or less, are described. The self-assembled gel compositions can encapsulate one or more agents. Methods of making the self-assembled gel compositions, and methods of drug delivery using the self-assembled gel compositions are also described.

33 Claims, 15 Drawing Sheets

(56) References Cited

FOREIGN PATENT DOCUMENTS

| FR | 2417494 | 9/1979 |
|---|---|---|
| WO | 9907416 | 2/1999 |
| WO | 2006008386 | 1/2006 |
| WO | 2010/033726 | 3/2010 |
| WO | 2010-033726 | 3/2010 |
| WO | 2012040623 | 3/2012 |
| WO | 2014089472 | 6/2014 |

OTHER PUBLICATIONS

Bhuniya et al., Tetrahedron Lett 47: 7153-7156 (2006) (Year: 2006).*
Kumar et al., Chem Commun 4059-4061 (2005) (Year: 2005).*
Esch et al., Angew Chem Int Ed 39: 2263-2266 (2000) (Year: 2000).*
Burns et al., "Physical Characterization and Lipase Susceptibility of Short Chain Lecithin/Triglyceride Mixed Micelles Potential Lipoprotein Models," J. Biol. Chem. 26:2716-2722 (1987).
European Search Report issued in EP11827647.6 dated Jul. 16, 2014 (6 pages).
Molinier et al., "PFGSE-NMR study of the self-diffusion of sucrose fatty acid monoesters in water," J. Colloid Interface Sci. 286(1):360-3688 (2005).
Palma et al., "Evaluation of the surfactant properties of ascorbyl palmitate sodium salts," Eur. J. Pharm. Sci. 16(1-2):37-43 (2002).
van Bommel et al., "Two-stage enzyme mediated drug release from LMWG hydrogels", Organic & Biomolecular Chemistry, 3(16):2917-2920 (2005).
International Search Report and Written Opinion dated Apr. 17, 2012 issued in international application No. PCT/US2011/053075, 9 pgs.
International Preliminary Report on Patentability issued in PCT/US2011/053075 dated Mar. 26, 2013, 6 pages.
Bennett, et al., "Next-generation hydrogel films as tissue sealants and adhesion barriers," Cardiac Surgery 18:494-9 (2003).
Bhattacharya, et al., "In Molecular Gels," Kluwer Academic Publishers: The Netherlands (2004).
Bhuniya, et al., "(S)-(+)-Ibuprofen-Based Hydrogelators: An Approach Toward Anti-Inflammatory Drug Delivery," Tetrahedron Lett. 47:7153-6 (2006).
Bong, et al., Angew. "Self-Assembling Organic Nanotubes," Chem. Int. 40:988-1011 (2001).
Bonte and Juliano, "Interactions of liposomes with serum proteins", Chem Phys Lipids, 40:359-72 (1986).
Boutaud, et al., J.A. "Determinants of the Cellular Specificity of Acetaminophen as an Inhibitor of Prostaglandin H(2) Synthases," PNAS, 99:7130-5 (2002).
Browne, et al., "Clinical outcome of autologous chondrocyte implantation at 5 years in US subjects", Clin Orthop Relat Res., 436:237-45 (2005).
Bryers, et al., "Biodegradtion of Poly(anhydride-esters) into Non-Steroidal Anti-Inflammatory Drugs and Their Effect on Pseudomonas aeruginosa Biofilms In Vitro and on the Foreign-Body Response In Vivo," Biomaterials, 27:5039-48 (2006).
Casuso, et al., "Converting drugs into gelators: supramolecular hydrogels from N-acetyl-L-cysteine and coinage-metal salts", Org Biomol Chem., 8:5455-8 (2010).
Choi, et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", J Materials Sci., 12:67-73 (2001).
Chourasia, et al., "Pharmaceutical Approaches to Colon-Targeted Drug Delivery Systems," Pharm. Pharmaceut. Sci., 6:22-66 (2003).
Donati, et al.,"Synergistic effects im semidilute mixed solutions of alginate and lactose-midified chitosam (chitlac)", Biomacromolecules, 8:957-62 (2007).

Erdmann, et al., "Degradable Poly(anhydridie ester) Implants: Effects of Localized Salicylic Acid Release on Bone," Biomaterials, 21:2507-12 (2000).
Estroff, et al., "Effective Gelation of Water Using a Series of Bis-urea Dicarboxylic Acids," Angew. Chem. Int. Ed. 39:3447-50 (2000).
Fischel-Ghodsian, et al., "Enzymatically Controlled Drug Delivery," PNAS. 85:2403-6 (1988).
Friggeri, et al., "Entrapment and release of quinoline derivatives using a hydrogel ofa low molecular weight gelator", Controlled Release 97: 241-8 (2004).
Gong, et al., "Synthesis ofhydrogels with extremely low surface friction", J. Am. Chem. Soc., 123:5582 (2001).
Gopinath, et al., "Ascorbyl palmitate vesicles (aspasomes): formation characterization and applications", Intl J Pharma., 271(1-2):95-113 (2004).
Gupta, et al., "Hydrogels.from controlled release to pH-responsive drug delivery", Drug Discovery Today, 7:569-79 (2002).
Han, et al., "Catalytic ester-amide exchange using group (iv) metal alkoxide-activator complexes", JACS, 127:10039-44 (2005).
Hans, et al., "Synthesis and characterization ofmPEG-PLA prodrug micelles", Biomacromolecules, 6, 2708-17 (2005).
Harten, et al., "Salicylic acid-derived poly(anhydride-esters) inhibit bone resorption and formation in vivo", Biomed. Mater. Res-A 72A:354-62 (2005).
Hoare, et al., ,,Hydrogelsin drug delivery: Progress and challenges, Polymer, 49:1993-2007 (2008).
Huang, et al., "On the importance and mechanisms of burst release in matrix-controlled drug delivery svstems", Controlled Release, 73: 121-36 (2001).
Hunziker, "Articular cartilage repair: basic science and clinical progress. A review of the current status and prospects", Osteoarthritis Cartilage, 10:432-63 (2002).
Indomethacin, MSDS product information, copywright Jun. 19, 2012.
International Search Report for PCT/US2009/057349 dated May 6, 2009.
International Search Report for PCT/US2016/031614 dated Jul. 26, 2017.
International Search Report for PCT/US2016/056070 dated Jan. 12, 2017.
International Search Report for PCT/US2017/031615 dated Sep. 25, 2017.
Jen, et al., "Review. Hydrogels for cell immobilization", Biotechnol. Bioeng.,50: 357-64 (1996).
John, et al., "Biorefinery. A design tool for molecular gelators," Langmuir. 26: 17843-51 (2010).
John, et al., "Enzymatically Derived Sugar-Containing Self-Assembled Organogels with Nanostructured Morphologies," Agnew. Chem. Int. Ed. 45:4772-5, 2006.
John, et al., "Lipid-based nanotubes asfunctional architectures with embedded fluorescence and recognition capabilities", J. Am. Chem. Soc., 126, 15012-13 (2004).
John, et al., "Morphological control of helical solid bilayers in high-axial-ratio nanostructures through binarv sell-assemble", Chem. Eur. J., 8:5494-500 (2002).
John, et al., "Unsaturation effect on gelation behavior ofaryl glycolipids", Langmuir, 20:2060-5 (2004b).
John, et al.,"Nanotube Formation from Renewable Resources via Coiled Nanofibers", AdV. Mater., 13:715-18 (2001).
Jovanovic, et al., "How curcumin works preferentially with water soluble antioxidants", Chem. Soc., 123, 3064-68 (2001).
Jung, et al., "Self-Assembly ofa Sugar-Based Gelator in Water. Its Remarkable Divers ity in Gelation Ability and Aggregate Structure, " Lanumuir 17, 7229-32 (2001).
Kalgutkar, et al., "Ester and Amide Derivatives of the Nonsteriodal Antiinflammatory Drug,Indomethacin, as selective cyclooxygenase-2 inhibitors," J. Med. Chem.,43:2860-70 (2000).
Kamath, et al., "Biodegradable Hydrogels in Drug Delivery," Adv. Drug Deliv. Rev., 11:59-84 (1993).
Kim, et al., "In vivo evaluation of polymeric micellar paclitaxel formulation. toxicity and efficacy", Controlled Release, 72: 191-202 (2001).

(56) References Cited

OTHER PUBLICATIONS

Kitagawa, et al., "Cationic Vesicles Consisting of 1,2-Dioleoyl-3-Trimethylammonium Propane (DOTAP) and Phosphatidylcholines and Their Interaction with Erythrocyte Membrane", Chem Pharma Bull., 52(4):451-3 (2004).
Kiyonaka, et al., Semi-wc/ peptide/protein array using supramolecular hydrogel, Nat. Mater., 3,58-64 (2004).
Kobayashi, et al., "Molecular design of "super" hydrogelators. understanding the gelation process of azobenzene-based sugar derivatives in water", Org. Lett. 4: 1423-6 (2002).
Kumar, et al. "Prodrugs as self-assembled hydrogels: a new paradigm for biomaterials, Biotech., 24:1-9 (2013.
Kumar, et al., "First snapshot of a nonpolymeric hydrogelator interacting with its getting solvents", Chem. Commun., 4059-62 (2005).
Lee, et al., "Hydrogelsfor Tissue Engineering," Chem. Rev., 101: 1869-80 (2001).
Li, et al., "Molecular nanofibers of olsalazine form supramolecular hydrogeis for reductive release of an anti-inflammatory agent, JACS, 132:17707-9 (2010).
Loos, et al., "Design and Application of Self-Assembled Low Molecular Weight Hydrogels," Eur. J.Organic Chem. 17:3615-31 (2005).
Lu, et al., "Photopolymerization ofmultilaminated poly(HEMA) hydrogels for controlled release", Controlled Release, 57:291-300 (1999).
Luboradzki, et al., "AnAttempt to Predict the Gelation Ability ofHydrogen-Bond-Based Gelators Utilizing a Glvcosidase Librarv," Tetrahedron 56:9595-9 (2000).
Magnussen, et al., "Treatment of focal articular cartilage defects in the knee: a systematic review", Clin Orthop Relat Res, 466:952-96 (2008).
Makarevic, et al., "Bis(amino acid) oxalyl amides as ambidextrous gelators of water and organicsolvents. supramolecular gels with temperature dependent assembly/dissolution equilibrium",Chem. Eur. J. 7:3328-41 (2001).
Marsich, et al., "Alginate/lactose-modified chitosan hydrogels: A bioactive biomaterial for chondrocyte encapsulation", J Biomat Mater Res A, 84(2):364-76 (2008).
Mazumdar, et al., "Preparation and evaluation ofethambutol derivatives," Indian J. Pharm. Sci., 47: 179-80 (1985).
Menger, et al., "Anatomy ofa Gel. Amino Acid Derivatives that Rigidify Water at Submillimolar Concentrations," J. Am. Chem. Soc. 122:11679-91 (2000).
Miyata, et al., "Biomolecule-Sensitive ydrogels," Adv. Drug Deliv. Rev., 54:79-98 (2002).
Nicolaou, et al., "A Water-Soluble Prodrug of Taxol with Self-Assembling Properties," Agew.Chem. Int. Ed., 33: 1583-7 (1994).
Oda, et al., "Gemini Surfactants as New, Low Molecular Weight Gelators of Organic Solvents and Water," Angew. Chem. Int. Ed. 37, 2689-91 (1998).
Peppas, "Hydrogels and Drug Delivery," Curr. Opin. Colloid Interface Sci. 2:531-7 (1997).
Peppas, et al., "Hydrogels in Biology and Medicine. From Molecular Principles to Bionanotechnologv," R. Adv. Mater., 18:1345-60 (2006).
Peppas, et al., "Hydrogels in pharmaceutical formulations," Eur. J. Pharm. Biopharm., 50:27-46 (2000).
Persico, et al.,"Effect of tolmetin glycine amide (McN-4366) a prodrug of tolmetin sodkum on adjuvant arthritis in the rat", J Pharma Exp Therap., 247(3):889-96 (1988).
Pietzyk, et al., "Degradation of phosphatidylcholine in liposomes containing carboplatin in dependence on composition and storage conditions", Intl J Pharma., 196(2):215-8 (2008).
Poulsen, et al., "Effect of topical vehicle composition on the in vitro release of fluocinolone acetonide and its acetate ester", J Pharma Sci., 57(6):928-33 (1968).
Preliminary Report on Patentability for PCT/US2011/053075 dated Mar. 26, 2013.
Qiu, et al., "Environment-sensitive hydrogels for drug dc/ivory," Adv. Drug Deliv. Rev., 53, 321-39 (2001).

Rattie, et al., "Acetaminophen Prodrugs III. Hydrolysis of Carbonate and Carboxylic Acid Esters in Aqueous Bu[[ers," J. Pharm. Sci., 59: 1738-41 (1970).
Robinson, et al., "Design, synthesis, and biological evaluation ofangiogenesis inhibitors. Aromatic cnonc and dienone analogues ofcurcumin", Bioru. Med. Chem. Lett., 13:115-17 (2003).
Rooseboom, et al., "Enzyme-catalyzed activation ofanticancer prodrugs", Pharmacol. Rev., 56:53-102 (2004).
Sinha, et al., "Microbially triggered drug delivery to the colon", Eur. J. Pharm. ScL, 18:3-18 (2003).
Sreenivasachary, et al., "Gelation-driven component selection in the generation of constitutional dynamic hydrogels based on guanine-quartet formation", PNAS, 102:5938-43 (2005).
Toth and Urtis, "Commonly used muscle relaxant therapies for acute low back pain: A review of carisoprodol cyclobenzaprine hydrochloride, and metaxalone", Clin Therap., 26(9):1355-67 (2004).
Trouet, et al., "Extracellularly tumor-activated prodrugs for the selective chemotherapy of cancer application to doxorubicin and preliminary in vitro and in vivo studies", Cancer Res., 61: 2843-6 (2001).
Troung, et al., "Self assembled gels for biomedical applications", Focus Rev., 6:30-42 (2011).
van der Linden, et al., "Clinic/us-scnsi/ivc hydrogels and their applications in chemical (micro)analvsis", Analyst, 128:325- 31 (2003).
Vassilev, et al., "Enzymatic Synthesis of a Chiral Gelator with Remarkably Low Molecular Weight," Chem. Commun., 1865-6 (1998).
Vemula, et al., "Encymc Catalysis. Tool to Make and Break Amygdalin Hydrogelators from Renewable Resources. A Delivery Model for Hydrophobic Drugs", J. Am. Chem. Soc., 128: 8932- 8 (2006).
Vemula, et al., "In Situ Synthesis of Gold Nanoparticles using Molecular Gels and Liquid Crystals from Vitamin-C Amphiphiles," Chem. Mater. 19, 138- 40 (2007).
Vemula, et al., "Smart Amphiphiles. Hydro/Organogelators for in Situ Reduction of Gold", Chem.Commun., 2218-20 (2006).
Vigroux, et al., "Cyclization-activated prodrugs: N-(substituted 2-hydroxyphenyl and 2-Hydroxypropyl)carbamates based on ring-opened derivatives of active benzoxazolones and oxazolidinones as mutual prodrugs of acetaminophen", J Med Chem., 38:3983-94 (1995).
Vohra, et al., "Nanolipi carrier-based thermoreversible gel for localized delivery of docetaxel to breast cancer", Cancer Nanotechnol., 4(1-3):1-12 (2013).
Wang, et al., "Low Molecular Weight Organogelators for Water," Chem. Commun. 310-11 (2003).
Wang, et al., "Hydrogels as separation agents responsive gels", Transitions II, Adv Polymer Sci., 110:67-79 (1993).
Whitesides, et al., "Beyond molecules. self-assembly ofmesoscopic and macroscopic components", PNAS 4769-74 (2002).
Xing, et al., J. "Hydrophobic Interaction and Hydrogen Bonding Cooperatively Confer a Vancomycin Hydrogel. A Potential Candidatefor Biomaterials," J. Am. Chem. Soc. 124:14846-7 (2002).
Yan, et al., "Enzymatic Production ofsugar Fatty Acids Esters," PhD thesis, University of Stuttgard, (2001).
Yang, et al., "A Simple Visual Assay Based on Small Molecule Hydrogels for Detecting Inhibitors of Prcrmcs," Chem. Commun., 2424-5 (2004).
Yang, et al., "Enzymatic Formation of Supramolecular Hydrogels," Adv. Mater., 16:1440-4 (2004b).
Yang, et al., "Enzymatic Hydrogelation ofsmall Molecules", Ace. Chem. Res., 41:315-26 (2008).
Yang, et al., "Small Molecular Hydrogels Based on a Class ofAnti-Inflammatory Agents," Chem. Commun., 208-9 (2004c).
Yang, et al., "Using a Kinase/Phosphatase Switch to Regulate a Supramolecular Hydrogel and Forming the Supramolecular Hvdrogel In Vivo," J. Am. Chem. Soc. 128:3038-43 (2006).
Zhang, et al., "An inflammation-targeting hydrogel for local drug delivery in inflammatory bowel disease", Sci Transl Med., 7(300):300ra128 (2015).

(56) References Cited

OTHER PUBLICATIONS

Zhang, et al., "Hydrogels: Wet or Let Die," Nature Materials 3:7-8 (2004).
Zhang, et al., "Self-assembled networks and molecular gels derived fro, long-chain, naturally-occurring fatty acids", J Brazilian Chem Soc., 239-55 (2016).
Zhang, et al., "Versatile small-moleule motifs for self-assemly in water and the formation of viofunctional supramolecular hydrogels", Langmuir, 27(2):529-37 (2011).

* cited by examiner

NANOSTRUCTURED GELS CAPABLE OF CONTROLLED RELEASE OF ENTRAPPED AGENTS

RELATED APPLICATIONS

This application claims the benefit of U.S. Provisional Application No. 61/386,268, filed on Sep. 24, 2010, and U.S. Provisional Application No. 61/466,753, filed on Mar. 23, 2011. The contents of each of these prior applications are incorporated herein by reference in their entireties.

TECHNICAL FIELD

This invention relates to self-assembled gels including gelators having a relatively small molecular weight, and more particularly to self-assembled gels including generally recognized as safe (GRAS) gelators.

REFERENCE TO SEQUENCE LISTING

The Sequence Listing submitted on Aug. 23, 2016, as a text file named "BWH_21124_MIT_15218_CON_ST25.txt," created on Jun. 28, 2016, and having a size of 1,066 bytes is hereby incorporated by reference pursuant to 37 C.F.R § 1.52(e)(5).

BACKGROUND

Local delivery of drugs can provide high local drug concentration while minimizing systemic toxicity, which can often be observed with oral dosing. However, as local depots are generally administered less frequently and include an initial burst followed by a continuous release, to maximize efficiency of therapy, it is desirable that a drug is only released when needed.

Delivering drugs to patients in a safe, effective, and compliant manner is a major challenge for the treatment of many types of disease. The ability of drugs to reach target tissues from the point of oral administration can be limited by multiple barriers including enzymatic and acidic degradation in the stomach, absorption across the intestinal epithelium, hepatic clearance, and nonspecific uptake. Effective oral dosing to achieve high concentrations of drugs within specific tissues while minimizing systemic toxicity can present a significant challenge. Conventional polymeric drug delivery systems such as implants, injectable microspheres, and patches are used by tens of millions of people annually, yet often produce a sharp initial increase in concentration to a peak above the therapeutic range, followed by a fast decrease in concentration to a level below the therapeutic range. Additionally, noncompliance with oral medication is a leading cause of hospitalizations.

The holy grail of drug delivery is an autonomous system that can titrate the amount of drug released in response to a biological stimulus, thereby ensuring that the drug is released when needed at a therapeutically relevant concentration. Such a system can rapidly release drug in response to fluctuations due to the severity of disease (this is often reflected by the local inflammatory state), patient-to-patient variability, and environmental factors.

SUMMARY

The disclosure relates, at least in part, to self-assembled gel compositions including one or more generally recognized as safe (GRAS) gelators. Substances and agents such as small molecular agents, drugs, drug-candidates, vitamins, proteins, dyes and sensors can be encapsulated within the assembled structures. The encapsulated substance or substances can be subsequently delivered through hydrolytic or other forms of degradation of the self-assembled gels or in response to an external stimulus, such as a specific enzyme. In some embodiments, the self-assembled gels can be formed of one or more amphiphilic gelators, which can encapsulate one or more different agents (e.g., therapeutic agents). The new amphiphilic gelators can act in synergy with the encapsulated agent, such that a therapeutic effect of the encapsulated agent is enhanced compared to a non-encapsulated agent. In some embodiments, self-assembled gels can encapsulate and release two or more different agents that can act synergistically to achieve enhanced efficacy. In some embodiments, self-assembled gels can include vitamins or vitamin derivatives in combination with either another vitamin derivative or a GRAS gelator. The self-assembled gels can increase stability of agents, such as encapsulated therapeutic agents and/or vitamins, e.g., from photo/ultra-violet degradation, and can deliver high concentrations of vitamins or GRAS agents.

The disclosure also relates, at least in part, to self-assembled hydrogel compositions including an enzyme-cleavable GRAS gelator, such as a GRAS gelator including a molecular weight of 2,500 or less. The hydrogel compositions can self-assemble under specific assembly conditions. Hydrogels can offer advantages such as the ability to hydrate in aqueous conditions and enhanced biological compatibility, and can be well suited for biological administration (e.g., implantation of wet hydrogels). Furthermore, the disclosure relates, at least in part, to organogels formed of GRAS gelators such as ascorbyl alkanoate, sorbitan alkanoate, triglycerol monoalkanoate, sucrose alkanoate, and/or glycocholic acid.

In one aspect, the disclosure features self-assembled gel compositions including enzyme-cleavable, generally recognized as safe (GRAS) first gelators having a molecular weight of 2500 or less. The GRAS first gelators can include ascorbyl alkanoate, sorbitan alkanoate, triglycerol monoalkanoate, sucrose alkanoate, glycocholic acid, and/or any combination thereof. The GRAS first gelators can self-assemble into gels including nanostructures.

In another aspect, the disclosure features self-assembled gel compositions capable of controlled release of agents. The self-assembled gel compositions include enzyme-cleavable, generally recognized as safe (GRAS) first gelators having a molecular weight of 2500 or less; and one or more agents, e.g., any agents as described herein. The GRAS first gelators can include ascorbyl alkanoate, sorbitan alkanoate, triglycerol monoalkanoate, sucrose alkanoate, glycocholic acid, and/or any combination thereof, and can self-assemble into gels including nanostructures. The agents can be encapsulated within or between the nanostructures, can be non-covalently bonded to the nanostructures, or both.

In yet another aspect, the disclosure features methods of forming self-assembled gel compositions. The methods include combining enzyme-cleavable generally recognized as safe (GRAS) gelators having a molecular weight of 2500 or less and solvents to form a mixture; heating or sonicating the mixture; stirring or shaking the mixture for a time sufficient to form a homogeneous solution; and cooling the homogeneous solution for a time sufficient to enable the formation of self-assembled gel compositions. The GRAS gelators can include ascorbyl alkanoate, sorbitan alkanoate, triglycerol monoalkanoate, sucrose alkanoate, glycocholic acid, and/or any combination thereof. In some embodiments, the methods further include lyophilizing self-assembled gels to form xerogels.

In another aspect, the disclosure features methods of forming a self-assembled gel composition. The methods include combining enzyme-cleavable generally recognized as safe (GRAS) first gelators having a molecular weight of 2500 or less and second gelators to form a mixture; heating or sonicating the mixture; stirring or shaking the mixture for a time sufficient to form a homogeneous solution; and cooling the homogenous solution for a time sufficient to enable the formation of self-assembled gel compositions. The GRAS first gelators can include ascorbyl alkanoate, sorbitan alkanoate, triglycerol monoalkanoate, sucrose alkanoate, glycocholic acid, and/or any combination thereof, and second gelators can include alpha tocopherol acetate, retinyl acetate, and/or retinyl palmitate. In some embodiments, the methods further include lyophilizing the self-assembled gel to form a xerogel.

In a further aspect, the disclosure features self-assembled gel compositions including amphiphilic 3-aminobenzamide derivatives having a molecular weight of 2500 or less. The amphiphilic 3-aminobenzaminde derivatives can self-assemble into gels comprising nanostructures. The self-assembled gel compositions can further include an agent, and the agent can be encapsulated within or between the nanostructures or non-covalently bonded to the nanostructures.

In yet a further aspect, the disclosure features self-assembled gel compositions including an enzyme-cleavable, generally recognized as safe (GRAS) first gelator having a molecular weight of 2500 or less and a non-independent second gelator. The first gelator and the non-independent second gelator each independently can have a concentration of from 0.01 to 20 percent by weight per gel volume. The GRAS first gelator can include ascorbyl alkanoate, sorbitan alkanoate, triglycerol monoalkanoate, sucrose alkanoate, glycocholic acid, and any combination thereof. The non-independent second gelator can include alpha tocopherol acetate, retinyl acetate, and retinyl palmitate.

Embodiments of the above-mentioned aspects can have one or more of the following features.

In some embodiments, the ascorbyl alkanoates include ascorbyl palmitate, ascorbyl decanoate ascorbyl laurate, ascorbyl caprylate, ascorbyl myristate, ascorbyl oleate, and/or any combination thereof. For example, the ascorbyl alkanoates can include ascorbyl palmitate. In some embodiments, the sorbitan alkanoates include sorbitan monostearate, sorbitan decanoate, sorbitan laurate, sorbitan caprylate, sorbitan myristate, sorbitan oleate, and/or any combination thereof. For example, the sorbitan alkanoate can include sorbitan monostearate. In some embodiments, the triglycerol monoalkanoates include triglycerol monopalmitate, triglycerol monodecanoate, triglycerol monolaurate, triglycerol monocaprylate, triglycerol monomyristate, triglycerol monostearate, triglycerol monooleate, and/or any combination thereof. For example, the triglycerol monoalkanoates include triglycerol monopalmitate. In some embodiments, the sucrose alkanoates include sucrose palmitate, sucrose decanoate, sucrose laurate, sucrose caprylate, sucrose myristate, sucrose oleate, and/or any combination thereof. For example, the sucrose alkanoates can include sucrose palmitate. In some embodiments, the GRAS first gelators include glycocholic acid.

In some embodiments, the self-assembled gel compositions include non-independent second gelators that can include alpha tocopherol acetate, retinyl acetate, and/or retinyl palmitate. The non-independent second gelators can co-assemble with the GRAS first gelators to form the self-assembled gels.

The self-assembled gel compositions can be solvent-free. When the self-assembled gels are solvent free, the gels can include from 0.5 (e.g., from one, from two, from three, from five, from 10, from 15, or from 20) to 25 (e.g., to 20, to 15, to 10, to five, to three, to two, or to one) percent by weight of the GRAS or non-GRAS first gelator and from 75 (e.g., from 80, from 85, from 90, from 95, from 97, from 98, or from 99) to 99.5 (e.g., to 99, to 98, to 97, to 95, to 90, to 85, or to 80) percent by weight of the non-independent second gelator. In some embodiments, the gel compositions can include independently from 0.01 (e.g., from 0.05, from 0.5, from one, from two, from three, from five, from 10, or from 15) to 25 percent (to 20, to 15, to 10, to five, to three, to two, to one, to 0.5, to 0.05) by weight per gel volume of the GRAS and/or of the non-independent second gelator.

In some embodiments, the self-assembled gel compositions can include a polar or non-polar solvent, such as water, benzene, toluene, carbon tetrachloride, acetonitrile, glycerol, 1,4-dioxane, dimethyl sulfoxide, ethylene glycol, methanol, chloroform, hexane, acetone, N, N'-dimethyl formamide, ethanol, isopropyl alcohol, butyl alcohol, pentyl alcohol, tetrahydrofuran, xylene, mesitylene, and/or any combination thereof. When the self-assembled gels include a solvent, the gels can include between 0.01 and 18 (e.g., between 0.05 and 18, between 0.01 and 15, between 0.05 and 15, between 0.1 and 15, between 0.5 and 15, between one and 15, or between one and 10) weight/volume percent of one or more generally recognized as safe gelators in the solvent.

In some embodiments, the nanostructures can include lamellae formed of the enzyme-cleavable GRAS first gelators. The agents (e.g., hydrophobic or hydrophilic) can be encapsulated between the lamellae. As an example, the agents can include a steroid, an anti-inflammatory agent, a chemotherapeutic, a PARP-inhibitor, a polypeptide, a nucleic acid, a polynucleotide, a polyribonucleotide, an anti-pain agent, an anti-pyretic agent, an anti-depression agent, a vasodilator, a vasoconstrictor, an immune-suppressant, a tissue regeneration promoter, a vitamin, a small interfering RNA, a polymer selected from the group consisting of poly(ethylene glycol), poly(ethylene oxide), hyaluronic acid, chitosan, carboxy methylcellulose, poly (ethylene glycol) di-acrylate, and poly(glycerol-co-sebasate acrylate), any derivative thereof, and/or any combination thereof. In some embodiments, when the self-assembled gel compositions include two or more agents, at least one agent potentiates an efficacy of one or more remaining agents.

In some embodiments, the amphiphilic 3-aminobenzamide derivatives can a structure of formula (I):

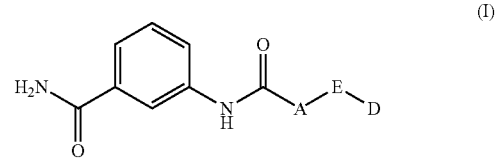

wherein
A is $CR_1R_2$ or O, wherein $R_1$ and $R_2$ are each independently H or halogen;
E is $C_{1-2}$ alkyl, $C_{1-2}$ haloalkyl, or absent;

D is selected from the group consisting of $C_{3-20}$ alkyl, $C_{2-6}$ alkenyl, aryl, $C_{3-20}$ cycloalkyl, wherein each are optionally substituted with 1, 2, 3, or 4 groups selected from the group consisting of $C_{1-4}$ alkoxy, $C_{1-8}$ alkyl, halo, $C_{1-8}$ haloalkyl, and nitro.

In some embodiments, the amphiphilic 3-aminobenzamide derivatives can be selected from:

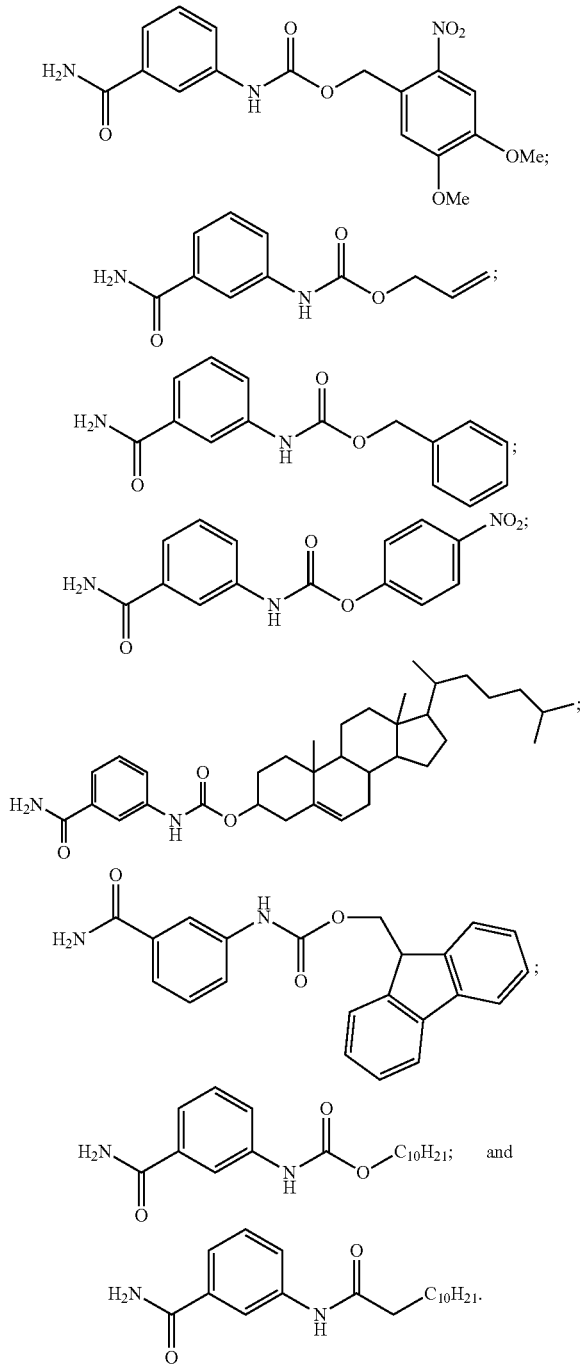

In some embodiments, when applied to a biological system, the amphiphilic 3-aminobenzamide derivatives can potentiates an efficacy (e.g., enhance the efficacy, and/or act synergistically with) of agents, such as chemotherapeutic agents (e.g., temozolomide, carmustine (bis-chloroethylnitrosourea), camptothecin, or and/paclitaxel).

When applied to a biological system, the self-assembled gel compositions described herein can provide controlled release of agents. The gel compositions can be adapted to be controllably disassembled.

In some embodiments, the self-assembled gel compositions are lubricious and/or have recoverable rheological properties. In some embodiments, the self-assembled gel compositions have an elastic modulus of from 10 to 10,000 Pascal and a viscous modulus of from 10 to 10,000 Pascal.

Embodiments and/or aspects can provide one or more of the following advantages.

The self-assembled gel compositions can enhance the stability and facilitate delivery of encapsulated agents or of gelators forming the gel. The self-assembled gel compositions can provide controlled release of an encapsulated agent, for example, upon exposure to a specific stimulus. The self-assembled gel compositions can act in synergy with an encapsulated agent, such that the efficacy of the agent is enhanced. In general, the gel compositions are relatively stable and easy to synthesize.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

Like reference symbols in the various drawings indicate like elements.

DETAILED DESCRIPTION

Figure 1:
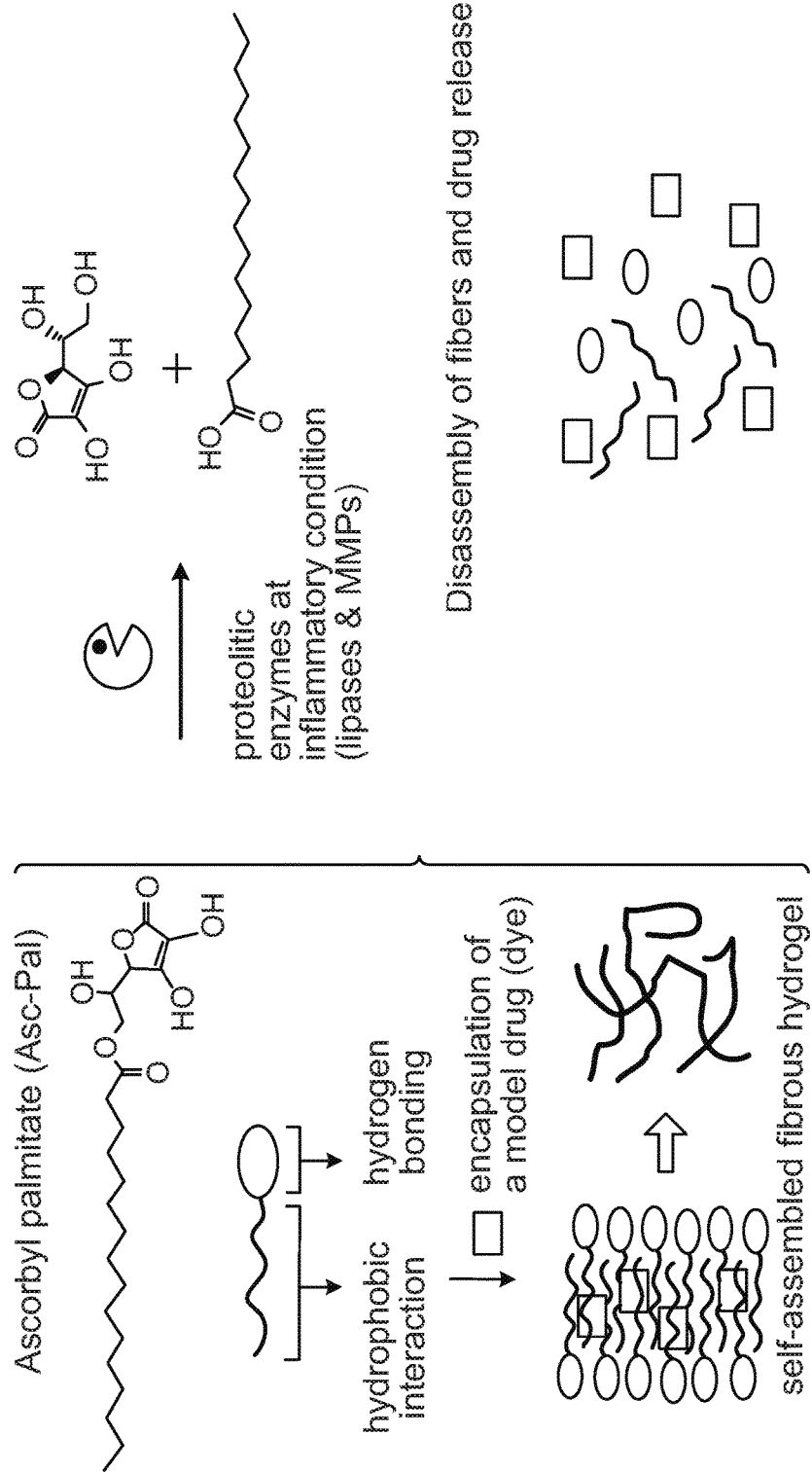
FIG. 1 is a graphical representation of a self-assembling gel composition, an agent encapsulation process, and a gel disassembly process.

There exist broad implications for achieving an on demand drug delivery approach for the treatment of tissue defects and multiple diseases. One approach toward this goal is the design of compounds tailored to release drugs in response to the local expression of enzymes that correlate with the level of inflammation. Inflammatory conditions that are characterized by the generation of enzymes that destroy extracellular connective tissue—such as occurs in rheumatoid arthritis (RA) and wound healing comprise a particularly attractive first application. By targeting other disease-associated enzyme pathways, this platform can have broad applicability for diseases such as cancer, ocular disease, oral disease, gastrointestinal disease, and cardiovascular disease.

Hydro- or organo-gel compositions as described herein consist of self-assembled macromolecular, nanostructure networks with a liquid filling the interstitial space of the network. The network holds the liquid in place through its interaction forces and so gives the gel solidity and coherence, but the gel is also wet and soft and capable of undergoing some extent of deformation. The gel state is neither solid nor liquid, but has some features of both. Self-assembly has been used to develop molecularly defined and functional materials, including hydrogels.

Self-assembled hydrogel compositions can be formulated in a variety of physical forms, including microparticles, nanoparticles, coatings and films. As a result, hydrogels are commonly used in clinical practice and experimental medicine for a wide range of applications, including tissue engineering and regenerative medicine, diagnostics, cellular immobilization, separation of biomolecules or cells and barrier materials to regulate biological adhesions. Hydrogel compositions are appealing for biological applications because of their high water content and biocompatibility.

Definitions

The term "$C_{2-6}$ alkenyl" denotes a group containing 2 to 6 carbons wherein at least one carbon-carbon double bond is present, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "$C_{1-4}$ alkoxy" as used herein denotes a group alkyl, as defined herein, attached directly to an oxygen atom. Examples include methoxy, ethoxy, n-propoxy, iso-propoxy, n-butoxy, t-butoxy, iso-butoxy, sec-butoxy and the like.

The term "alkyl" denotes a straight or branched carbon group containing 3 to 20 carbons, and some embodiments are 1 to 8 carbons. Examples of an alkyl include, but not limited to, methyl, ethyl, n-propyl, iso-propyl, n-butyl, secbutyl, iso-butyl, t-butyl, pentyl, iso-pentyl, t-pentyl, neopentyl, 1-methylbutyl (i.e., —CH(CH$_3$)CH$_2$CH$_2$CH$_3$), 2-methylbutyl (i.e., —CH$_2$CH(CH$_3$)CH$_2$CH$_3$), n-hexyl, lauryl, decanoyl, palmityl, caprylyl, myristyl, oleyl, stearyl and the like.

The term "C$_{1-2}$ alkylene" refers to a C$_{1-2}$ divalent straight carbon group. In some embodiments C$_{1-2}$ alkylene refers to, for example, —CH$_2$—, —CH$_2$CH$_2$—, and the like.

The term "aryl" denotes an aromatic ring group containing 6 to 14 ring carbons. Examples include phenyl, naphthyl, and fluorenyl.

The term "C$_{3-20}$ cycloalkyl" denotes a saturated ring group containing 3 to 20 carbons; some embodiments contain 3 to 17 carbons; some embodiments contain 3 to 4 carbons. Examples include cyclopropyl, cyclobutyl, cyclopentyl, cyclopenyl, cyclohexyl, cycloheptyl and the like.

The term "halogen" or "halo" denotes to a fluoro, chloro, bromo or iodo group.

The term "C$_{1-2}$ haloalkyl" denotes an C$_{1-2}$ alkyl group, defined herein, wherein the alkyl is substituted with one halogen up to fully substituted and a fully substituted C$_{1-2}$ haloalkyl can be represented by the formula C$_n$L$_{2n+1}$ wherein L is a halogen and "n" is 1, or 2; when more than one halogen is present then they may be the same or different and selected from the group consisting of F, Cl, Br and I, preferably F. Examples of C$_{1-2}$ haloalkyl groups include, but not limited to, fluoromethyl, difluoromethyl, trifluoromethyl, chlorodifluoromethyl, 2,2,2-trifluoroethyl, pentafluoroethyl and the like.

The term "C$_{1-8}$ haloalkyl" denotes an C$_{1-2}$ alkyl group, defined herein, wherein the alkyl is substituted with one halogen up to fully substituted and a fully substituted C$_{1-2}$ haloalkyl can be represented by the formula C$_n$L$_{2n+1}$ wherein L is a halogen and "n" is 1, 2, 3, 4, 5, 6, 7, or 8; when more than one halogen is present then they may be the same or different and selected from the group consisting of F, Cl, Br and I, preferably F.

The term "nitro" refers to the group —NO$_2$.

A "non-independent gelator" is a molecule that cannot, by itself, form a self-assembled gel, but can form an integral part of a self-assembled gel in the presence of another gelator that can promote gelation of the non-independent gelator, such as a GRAS gelator. The non-independent gelator forms part of the gel structure (e.g., a lamellar structure) with the gelator that promotes gelation of the non-dependent gelator. The non-independent gelator can be amphiphilic, having a hydrophilic group attached to a hydrophobic group, which can co-assemble with other hydrophilic and hydrophobic groups of an accompanying gelator molecule to form the gel structure.

"Hydrogels," as known to those of skill in the art, are 3-D networks of molecules typically covalently (e.g., polymeric hydrogels) or non-covalently (e.g., self-assembled hydrogels) held together where water is the major component (usually greater than 80%). Gels can be formed via self-assembly of gelators or via chemical crosslinking of gelators. Water-based gelators can be used to form hydrogels, whereas organogelators are gelators that form gels (organogels) in solvents where organic solvents are the major component.

"Organogels," as known to those of skill in the art, are 3-D networks of molecules typically covalently (e.g., polymeric hydrogels) or non-covalently (e.g., self-assembled hydrogels) held together where an organic solvent is the major component (usually greater than 80%). Gels can be formed via self-assembly of gelators or via chemical crosslinking of gelators.

"Gelators," as known to those of skill in the art, are molecules that can self-assemble through non-covalent interactions, such as hydrogen-bonding, van der Waals interactions, hydrophobic interactions, ionic interactions, pi-pi stacking, or combinations thereof, in one or more solvents. The gelators can form a gel by rigidifying the solvent through, for example, capillary forces. Gelators can include hydrogelators (e.g., gelators that form hydrogels) and organogelators (e.g, gelators that form organogels). In some embodiments, gelators can form both hydrogels and organogels.

Self-Assembled Gel Compositions

Generally, self-assembled gel compositions can include an amphiphilic gelator having a molecular weight of 2500 or less, such as an enzyme-cleavable, generally recognized as safe (GRAS) gelator having a molecular weight of 2500 or less. The generally recognized as safe gelator can include any agent listed on the FDA's GRAS list. For example, the GRAS gelator can include, but is not limited to, agents that are generally recognized, among experts qualified by scientific training and experience to evaluate their safety, as having been adequately shown through scientific procedures (or, in the case of a substance used in food prior to Jan. 1, 1958, through either scientific procedures or through experience based on common use in food) to be safe.

Without wishing to be bound by theory, it is believed that when amphiphilic molecules self-assemble in a solvent, hydrophobic and hydrophilic portions of the gelator molecules can interact to form lamellae of gelator molecules. In some embodiments, when the gels are hydrogels, the hydrophobic portions of gelators are located in the inner regions of a given lamella, and hydrophilic portions are located at the outer surfaces of the lamella. In some embodiments, when the gels are organogels, the hydrophobic portions of gelators are located in the outer regions of a given lamella, and hydrophilic portions are located at the inner surfaces of the lamella. The lamella can have a width of from about three (e.g., from about four) to about five (e.g., to about four) nanometers and a length of several microns (e.g., one micron, two microns, three microns, four microns, five microns, ten microns, twenty microns, or twenty five microns) or more. Several tens or hundreds of such lamellae can bundle together to form nanostructures, such as fibers and sheet-like structures. In some embodiments, the nanostructures can include nanoparticles, micelles, liposome vesicles, fibers, and/or sheets. In some embodiments, The nanostructures can have a minimum dimension (e.g., a thickness, a width, or a diameter) of 2 nm or more (e.g., 50 nm or more, 100 nm or more, 150 nm or more, 200 nm or more, 250 nm or more, 300 nm or more, 350 nm or more) and/or 400 nm or less (e.g., 350 nm or less, 300 nm or less, 250 nm or less, 200 nm or less, 150 nm or less, 100 nm or less, or 500 nm or less). In some embodiments, the nanostructures (e.g, fibers, sheets) can have a length and/or width of several microns (e.g., one micron, two microns, three microns, four microns, five microns, ten microns, twenty microns, or twenty five microns) or more. The nanostructures can aggregate into networks, and/or be in the form of a liquid crystal, emulsion, fibrillar structure, or tape-like morphologies. When the nanostructures are in the form of fibers, the fibers can have a diameter of about 2 nm or more, and can have lengths of hundreds of nanometers or more. In some embodiments, the fibers can have lengths of several microns (e.g., one micron, two microns, three microns, four microns, five microns, ten microns, twenty microns, or twenty five microns) or more.

In some embodiments, the GRAS gelators can include ascorbyl alkanoate, sorbitan alkanoate, triglycerol monoalkanoate, sucrose alkanoate, glycocholic acid, or any combination thereof. The alkanoate can include a hydrophobic $C_1$-$C_{22}$ alkyl (e.g., acetyl, ethyl, propyl, butyl, pentyl, caprylyl, capryl, lauryl, myristyl, palmityl, stearyl, arachidyl, or behenyl) bonded via a labile linkage (e.g., an ester linkage) to an ascorbyl, sorbitan, triglycerol, or sucrose molecule. For example, the ascorbyl alkanoate can include ascorbyl palmitate, ascorbyl decanoate, ascorbyl laurate, ascorbyl caprylate, ascorbyl myristate, ascorbyl oleate, or any combination thereof. The sorbitan alkanoate can include sorbitan monostearate, sorbitan decanoate, sorbitan laurate, sorbitan caprylate, sorbitan myristate, sorbitan oleate, or any combination thereof. The triglycerol monoalkanoate can include triglycerol monopalmitate, triglycerol monodecanoate, triglycerol monolaurate, triglycerol monocaprylate, triglycerol monomyristate, triglycerol monostearate, triglycerol monooleate, or any combination thereof. The sucrose alkanoate can include sucrose palmitate, sucrose decanoate, sucrose laurate, sucrose caprylate, sucrose myristate, sucrose oleate, or any combination thereof. In some embodiments, the GRAS gelators include ascorbyl palmitate, sorbitan monostearate, triglycerol monopalmitate, sucrose palmitate, or glycocholic acid.

In some embodiments, the self-assembled gel compositions can include one or more non-independent second gelators, such as a vitamin derivative, that is or are different from a GRAS gelator. For example, self-assembling gels can be formed of vitamins or vitamin derivatives in combination with another vitamin derivative, a GRAS gelator, or a non-GRAS gelator. The non-independent gelators cannot assemble into a gel by itself. However, the use of a first gelator, such as a GRAS first gelator, can promote the gelation of a non-independent second gelator, such that both the first and second gelators can co-assemble into a gel and can both be integrated into the gel structure (e.g., lamellar, micellar, vesicular, or fibrous structures), where neither gel components are merely encapsulated by the gel. In the case of non-independent vitamin gelator derivatives, the resulting gels can increase resistance to photo/ultra-violet degradation of vitamins and deliver high concentrations of vitamins or GRAS gelators.

In some embodiments, the non-independent second gelators include a liquid amphiphile. For example, the non-independent second gelators can include alpha tocopherol acetate, retinyl acetate, and/or retinyl palmitate. When the non-independent second gelators are liquid amphiphiles, the resulting gels can include a solvent, or be solvent-free. When the gels are solvent-free, the gels can include from 0.5 (e.g., from one, from two, from three, from five, from 10, from 15, or from 20) to 25 (e.g., to 20, to 15, to 10, to five, to three, to two, or to one) percent by weight of the GRAS or non-GRAS first gelator and from 75 (e.g., from 80, from 85, from 90, from 95, from 97, from 98, or from 99) to 99.5 (e.g., to 99, to 98, to 97, to 95, to 90, to 85, or to 80) percent by weight of the non-independent second gelator. When the gels includes a solvent, the gels can include, independently, from 0.01 (e.g., from 0.05, from 0.5, from one, from two, from three, from five, from 10, or from 15) to 25 percent (to 20, to 15, to 10, to five, to three, to two, to one, to 0.5, to 0.05) by weight per gel volume of the GRAS or non-GRAS first gelator and the non-independent second gelator. The resulting gels can be relatively stable and provide enhanced stability of the gel constituents (e.g., vitamin E and/or vitamin A derivatives).

In some embodiments, the self-assembled gel compositions include a solvent. Examples of solvents include water, benzene, toluene, carbon tetrachloride, acetonitrile, glycerol, 1,4-dioxane, dimethyl sulfoxide, ethylene glycol, methanol, chloroform, hexane, acetone, N, N'-dimethyl formamide, ethanol, isopropyl alcohol, butyl alcohol, pentyl alcohol, tetrahydrofuran, xylene, mesitylene, or any combinations thereof. When the self-assembled gels include a solvent, the gels can include between 0.01 and 18 (e.g., between 0.05 and 18, between 0.01 and 15, between 0.05 and 15, between 0.1 and 15, between 0.5 and 15, between one and 15, or between one and 10) weight/volume percent of the generally recognized as safe gelator in the solvent. For example, the gels can include from 0.5 to 25 percent by weight of the GRAS first gelator and 0.5 to 25 percent by weight of the non-independent second gelator.

In some embodiments, the self-assembled gel compositions are lyophilized to remove a solvent, such that the resulting gels form xerogels. Xerogels can be in a powder form, which can be useful for inhalation or for formation into pills for oral administration. As xerogels are solvent free, they can have improved shelf-life and can be relatively easily transported and stored. To lyophilize self-assembled gels, the gels can be frozen (e.g., at −80° C.) and vacuum-dried over a period of time to provide xerogels.

In some embodiments, instead of or in addition to a GRAS first gelator, the self-assembled gel compositions can be formed of amphiphilic 3-aminobenzamide derivatives including a molecular weight of 2,500 or less. The 3-aminobenzamide derivatives can form nanostructures having a maximum dimension of 2 nm or more (see, supra). The 3-aminobenzamide derivatives can further one or more agents encapsulated within the nanostructures or non-covalently bonded to the nanostructures.

In some embodiments, the amphiphilic 3-aminobenzamide derivatives have a structure of formula (I):

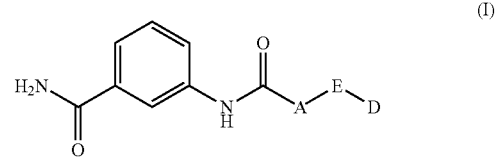

wherein

A is $CR_1R_2$ or O, wherein $R_1$ and $R_2$ are each independently H or halogen;

E is $C_{1-2}$ alkylene, $C_{1-2}$ haloalkyl, or absent;

D is selected from the group consisting of $C_{3-20}$ alkyl, $C_{2-6}$ alkenyl, aryl, $C_{3-20}$ cycloalkyl, wherein each are optionally substituted with 1, 2, 3, or 4 groups selected from the group consisting of $C_{1-4}$ alkoxy, $C_{1-8}$ alkyl, halo, $C_{1-8}$ haloalkyl, and nitro.

In some embodiments, A is $CH_2$ or O.

In some embodiments, E is $CH_2$ or $CH_2CH_2$.

In some embodiments, D is phenyl, optionally substituted with 1, 2, 3, or 4 groups selected from nitro and $C_{1-4}$ alkoxy.

In some embodiments, D is phenyl, optionally substituted with 1, 2, 3, or 4 groups selected from nitro and methoxy.

In some embodiments, D is ethylenyl.

In some embodiments, A is O; E is absent; and D is $C_{3-20}$ cycloalkyl, optionally substituted with 1, 2, 3, or 4 $C_{1-8}$ alkyl.

In some embodiments, A is $CH_2$ or O; E is absent, and D is $C_{3-20}$ alkyl.

In some embodiments, the amphiphilic 3-aminobenzamide derivative has a structure of formula (I):

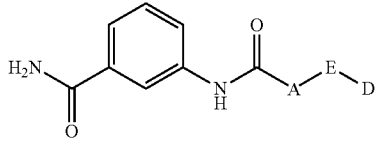

wherein

A is CH$_2$ or O;

E is CH$_2$, CH$_2$CH$_2$, or absent; and

D is selected from the group consisting of C$_{3-20}$ alkyl, C$_{3-20}$ cycloalkyl, ethylenyl, and phenyl, each optionally substituted with 1, 2, 3, or 4 groups selected from nitro, C$_{1-4}$ alkoxy, and C$_{1-8}$ alkyl.

In some embodiments, the amphiphilic 3-aminobenzamide derivatives can include:

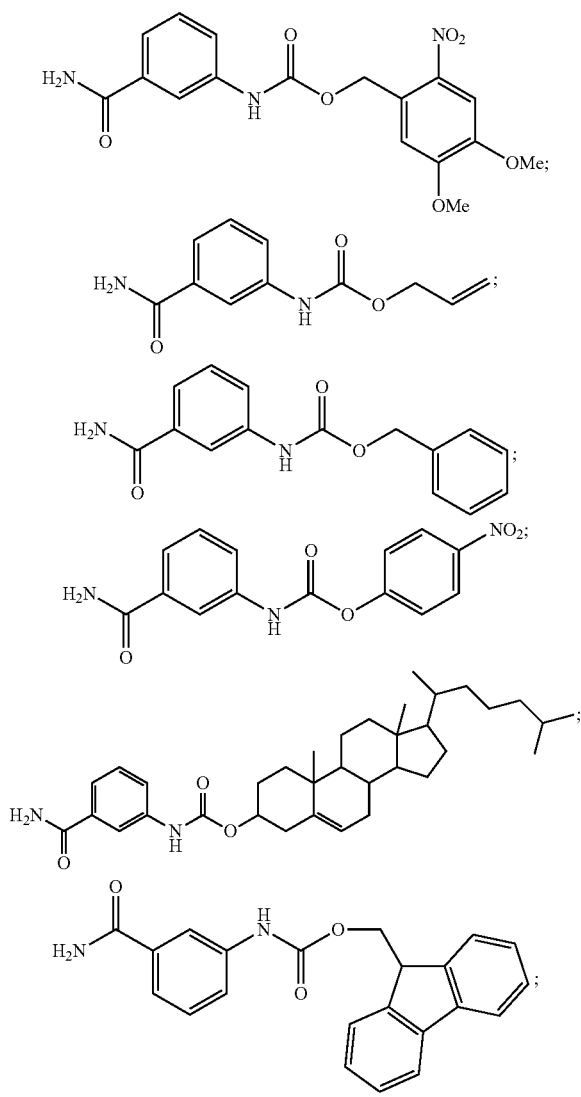

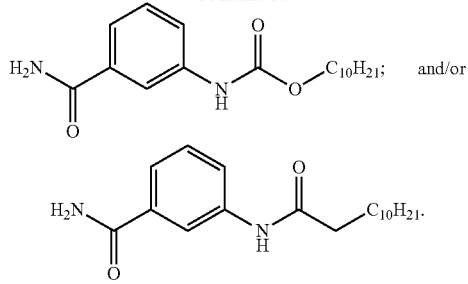

Self-Assembled Gel Compositions for Delivering Agents

In some embodiments, the self-assembled gel compositions can include one or more encapsulated agents. The agents can be hydrophobic, such the agents can be relatively non-polar and thus prefer neutral molecules and non-polar solvents. In some embodiments, the agents can be hydrophilic. The agents can have a molecular weight of less than or equal to about 500,000 Da. As an example, the agents can include a steroid, an anti-inflammatory agent, a chemotherapeutic, a polypeptide, a nucleic acid, a polynucleotide, a polyribonucleotide, an anti-pain agent, an anti-pyretic agent, an anti-depression agent, a vasodilator, a vasoconstrictor, an immune-suppressant, a tissue regeneration promoter, a vitamin, a vitamin derivative, a dye, a sensor, and/or a small interfering RNA. In some embodiments, the agents can include a polymer, such as poly(ethylene glycol), poly(ethylene oxide), hyaluronic acid, chitosan, carboxy methylcellulose, poly(ethylene glycol) di-acrylate, and poly(glycerol-co-sebasate acrylate), and/or any derivative thereof. In some embodiments, the agents include triamcinolone acetonide, dexamethasone, ethambutol, iodomethacin, camptothecin, paclitaxel, temozolomide, carmustine, PARP-inhibitors, and/or any derivative thereof. The encapsulated agents can be embedded between the lamellae of a self-assembled gel, or embedded within the hydrophobic groups of the gelators forming the self-assembled gel.

In some embodiments, the encapsulated PARP-inhibitors include NU1025, BSI-201, AZD-2281, ABT-888, AGO-14699, 4-hydroxyquinazoline, 3-aminobenzamide, 1,5-isoquinolinediol, 4-amino-1,8-napthalimide, O$^6$-benzylguanine, and/or derivatives thereof.

In some embodiments, the agents can include insulin, an anticoagulant, a blood thinner, an antioxidant, a sleep medication, an enzyme inhibitor, a GPCR agonist or antagonists, a vaccine, an inhibitory ribonucleic acid (RNAi), a protein, a peptide, an enzyme a nutrition supplement, an antibody, and/or an aptamers. In some embodiments, the agents can promote cell migration, proliferation, matrix production, cell differentiation, transendothelial migration, transdifferentiation, re-programming, and/or anti-apoptosis. In certain embodiments, the agents can alter metabolism.

Methods of Making the Self-Assembled Gel Compositions

Generally, to form a self-assembled gel composition, a solvent, a gelator, and optionally an agent to be encapsulated are added to a container to form a mixture. In some embodiments, the mixture can include one or more solvents, one or more gelators (e.g., GRAS gelators), and/or one or more agents to be encapsulated. The mixture can be heated and/or sonicated and/or placed in a bath to completely dissolve the gelator to form a homogeneous solution, and the solution is then cooled and/or rested in an undisturbed location. The solution can transition into a viscous gel after a given time period. Gelation is deemed complete when no gravitational flow is observed upon inversion of the container. To remove an unencapsulated agent from the gels, the gels can be repeatedly vortexed in a solvent that can dissolve the agent but that does not interact with the gels. The supernatant solution can be removed to extract any unencapsulated agent.

When the self-assembled gel compositions do not include a solvent, a gelator (e.g., a GRAS or a non-GRAS gelator) can be combined with a liquid amphiphile (e.g., a non-independent vitamin-derived liquid amphiphile) to form a mixture. The mixture can include one or more gelators and one or more liquid amphiphiles. The mixture is then heated/sonicated/placed in a bath to form a homogenous solution. The resulting solution is then allowed to cool and/or rest in an undisturbed location. The solution can transition into a viscous gel after a given time period.

In some embodiments, one or more gelators and optionally an agent to be encapsulated can be combined in the absence of a solvent to form a mixture. The mixture is then heated/sonicated/placed in a bath to form a homogenous solution. The resulting solution is then allowed to cool and/or rest in an undisturbed location. The solution can transition into a viscous gel after a given time period.

In some embodiments, to encapsulate an agent, a melted gel including one or more gelator and one or more solvents can be added to a solid agent, to an agent dissolved a the same one or more solvents, or to an agent dissolved or suspended in a gel-compatible solvent.

In some embodiments, the heating temperatures can be from 40 (e.g., from 50, from 60, from 70, from 80, from 90, or from 100) to 110 (e.g., to 100, to 90, to 80, to 70, to 60, or to 50° C. The mixtures can be heated and/or sonicated and/or placed in a bath for a duration of from one (e.g., from five, from 10, from 15, from 20, or from 25) to 30 (to 25, to 20, to 15, to 10, or to five) minutes. The solutions can be cooled to a temperature of from 4 (e.g., from 10, from 20, or from 25) to 37 (e.g., to 25, to 20, or to 10° C. and/or rested for a duration of from 15 minutes (e.g., from 30 minutes, from 45 minutes) to one hour (e.g., to 45 minutes, to 30 minutes).

As an example, 0.01-10 wt % of a GRAS first gelator and 0.01-10 wt % of GRAS second gelator can be dissolved in dissolved in 1-150 µl of water miscible organic solvent, optionally, 50-199 µl of either water or phosphate buffer saline (PBS) can be added to the mixture. Heating (40-110° C.) and/or sonication and/or placing in a bath for 1-30 min followed by cooling (4-37° C.) can occur to form assembled gels. In some embodiments, instead of GRAS gelators, one or more amphiphilic vitamin derivatives (e.g., a vitamin C ester, a vitamin A ester, a vitamin E ester) can be used.

As another example, 0.01-10 wt % of a GRAS first gelator, 0.01-10 wt % of a GRAS second gelator, and 0.01-8 wt % an agent of interest can be dissolved in 1-150 µl of water miscible organic solvent, subsequently 50-199 µl of either water or phosphate buffer saline (PBS) was added. Heating (40-110° C.) and/or sonication and/or placing in a bath for 1-30 min followed by cooling (4-37° C.) GRAS agent can occur to form assembled gels including an encapsulated agent. In some embodiments, the GRAS gelators can be dissolved in 1-150 µl of water miscible organic solvent, and an agent of interest (e.g., 0.1-5 wt %, 0.01-8 wt %) in water or PBS can be added to the GRAS gelator solution. In some embodiments, instead of GRAS gelators, one or more amphiphilic vitamin derivatives (e.g., a vitamin C ester, a vitamin A ester, a vitamin E ester) can be used.

When one gelator is a liquid, as an example, 0.01-15 wt % of a solid GRAS gelator and optionally 0.1-10 wt % of an agent of interest can be added to a liquid GRAS gelator, or the gelators and the agent of interest can be dissolved in an water miscible or immiscible organic solvent. In some embodiments, instead of GRAS gelators, one or more amphiphilic vitamin derivatives (e.g., a vitamin C ester, a vitamin A ester, a vitamin E ester) can be used.

As another example, 0.01-15 wt % of an amphiphilic GRAS-agent and 0.01-10 wt % of phospholipid (either cationic, or anionic, or zwitterionic) and 0.01-8 wt % of an agent of interest can be dissolved in an organic (water miscible or immiscible) solvent by heating (40-110° C.) and/or sonication and/or placing in a bath for 1-30 min, followed by cooling to lower temperature (4-37° C.) to form self-assembled organogels.

In some embodiments, 0.01-15 wt % of an amphiphilic GRAS gelator and 0.01-10 wt % of polymer (either cationic, anionic or zwitterionic or neutral) can be dissolved in 1-150 µl of a water miscible solvent, subsequently 50-199 µl of either water or phosphate buffer saline (PBS) was added to form a mixture. Heating (40-110° C.) and/or sonication and/or placing in a bath the mixture for 1-30 min, followed by cooling to lower temperature (4-37° C.) can provide self-assembled hydrogels. The mixture can optionally include 0.01-8 wt % of an agent of interest, dissolved in the water-miscible solvent, in the water, or PBS. In some embodiments, instead of a water miscible solvent, water, and/or PBS, the amphiphilic GRAS gelator, polymer, and/or agent of interest can be dissolved in a water miscible or immiscible organic solvent.

In some embodiments, self-assembled fibers are isolated through repeated cycles of centrifugation (2000-25000 rpm for 2-15 min) and PBS washings, to provide water dispersible self-assembled fibers with varying overall charge of the fibers.

Characteristics of Self-Assembled Gel Compositions, Uses, and Methods of Delivery The self-assembled gel compositions can be lubricious, such that when the gel compositions are administered to a surface, decreased wear is caused to the surface by a given friction-inducing object in a given amount of time. The self-assembled gel compositions can have recoverable rheological properties. For example, they can have an elastic modulus of from 10 (e.g., from 100, from 1,000, from 2,500, from 5,000, or from 7,500) to 10,000 (e.g., to 7,500, to 5,000, to 2,500, to 1,000, or to 100) pascals and a viscous modulus of from 10 (e.g., from 100, from 1,000, from 2,500, from 5,000, or from 7,500) to 10,000 (to 7,500, to 5,000, to 2,500, to 1,000, or to 100) pascals.

When administered to a biological system, the gel compositions can be controllably disassembled, for example, upon exposure to hydrolytic, enzymatic degradation conditions, or an external stimulus. Gel assembly can include cleavage of a labile linkage in an amphiphilic gelator, such as an ester, amide, anhydride, carbamate, phosphate-based linkages (e.g., phosphodiester), disulfide (—S—S—), acid-cleavable groups such as —OC(O)—, —C(O)O—, or —C=NN— that can be present between a hydrophobic and hydrophilic group within the gelator. Examples of labile linkages are also described, for example, in PCT publication WO2010/033726, herein incorporated by reference in its entirety.

In some embodiments, encapsulated agents can be controllably released from the gel compositions upon gel disassembly. For example, encapsulated agents can be gradually released over a period of time (e.g., a day, a week, a month, six months, or a year). Depending on the parameters, the release can be delayed from minutes to days to months or even years, for example, when gel compositions are administered under physiological conditions (a pH of about 7.4 and a temperature of about 37° C.). For example, the sustained release can be controlled by the concentration of an enzyme and/or a temperature. For instance, sustained release can be accelerated via high enzyme concentration. In some embodiments, the sustained release is delivered without a burst release, or with only a minimal burst release.

The stimuli can be found in biological systems. For example, in certain embodiments, gel compositions can be disassembled under biological conditions, e.g., conditions present in the blood or serum, or conditions present inside or outside the cell, tissue or organ. The gel compositions can be disassembled only under conditions present in a disease state of a cell, tissue or organ, e.g., inflammation, thus allowing for release of an agent at targeted tissue and/or organ. For example, the gel compositions can include degradable linkages that are cleavable upon contact with an enzyme and/or through hydrolysis, such as ester, amide, anhydride, and carbamate linkages. In some embodiments, phosphate-based linkages can be cleaved by phosphatases. In some embodiments, labile linkages are redox cleavable and are cleaved upon reduction or oxidation (e.g., —S—S—). In some embodiments, degradable linkages are susceptible to temperature, for example cleavable at high temperature, e.g., cleavable in the temperature range of 37-100° C., 40-100° C., 45-100° C., 50-100° C., 60-100° C., 70-100° C. In some embodiments, degradable linkages can be cleaved at physiological temperatures (e.g., from 36 to 40° C., about 36° C., about 37° C., about 38° C., about 39° C., about 40° C.). For example, linkages can be cleaved by an increase in temperature. This can allow use of lower dosages, because agents are only released at the required site. Another benefit is lowering of toxicity to other organs and tissues. In certain embodiments, stimuli can be ultrasound, temperature, pH, metal ions, light, electrical stimuli, electromagnetic stimuli, and combinations thereof.

When the self-assembled gel compositions include amphiphilic 3-aminobenzamide derivatives, the gel compositions can include encapsulated agents such as those discussed herein, and/or chemotherapeutic agents including temozolomide, carmustine, camptothecin, and/or paclitaxel. The amphiphilic 3-aminobenzamide derivatives, which are poly(ADP-ribose) ("PARP") inhibitors, can enhance (e.g., potentiate) the efficacy of encapsulated agents. For example, amphiphilic 3-amino benzamides can act in synergy with encapsulated agents by acting via complementary pathways in a biological system. The self-assembled gel compositions can also be internalized by cells—such that biologically active gelators (e.g., amphiphilic 3-aminobenzamide) can be released together with encapsulated agents at the same location within a biological system. Gelators and encapsulated agents that can act synergistically can include, for example, self-assembled gel compositions including vitamin C derivative gelators (e.g., ascorbyl alkanoate to increase iron absorption) and aloe (to increase absorption of vitamin C and E) which together can increase vitamin uptake; self-assembled gel compositions including PARP inhibitor gelators (e.g., amphiphilic 3-aminobenzamide) and cisplatin and/or BMS-536924 which together can block cellular repair pathways; self-assembled gel compositions including non-independent vitamin A derived gelators (e.g., retinyl acetate, retinyl palmitate) and interferons can provide heightened immune response; self-assembled gel compositions including a vitamin C derivative gelators (e.g., ascorbyl alkanoate) and vitamin K3 can increase the death of cancer cells; self-assembled gel compositions including non-independent vitamin E derived gelators (e.g., alpha tocopherol acetate) and vitamin D can promote remyelination.

The self-assembled gel compositions, which can optionally include encapsulated agents, can be used for treatment of a variety of conditions, such as proteolytic diseases, including inflammatory disease. In some embodiments, the gel compositions can be used as lubricants or viscosupplements to damaged joints. The gel compositions can restore lubricant properties of synovial fluid of arthritis/pathological joints. In some embodiments, the gel compositions can be used for replacement of fluids such as synovial fluid, aqueous humor, and/or vitreous humor. When gel compositions include encapsulated insulin, the gel compositions can be used for the treatment of diabetes.

In some embodiments, the self-assembled gel compositions can be used for cellular applications including cell delivery. The gel compositions can be used for of delivery osteogenic agents to promote osteogenesis, as part of an oral rinse to target the oral cavity, applied to the skin to release agents for cosmetic or therapeutic purposes, used to treat ulcers including mucosal and skin, used to treat tumors (examples may include brain, skin, head and neck, breast, prostate, liver, pancreas, lung, bone, and/or oral), used to treat acute and chronic kidney disease, and/or applied to treat gum disease. The gel compositions can be components in tooth paste, shampoo/conditioner, soap, shaving cream, hand cream, sanitizer, makeup, eye drops, razors, nasal spray, nail polish, hair spray/gel, shoe polish, paint, detergent, fabric softener, water purification, plaster, toilet cleaner, food. In some embodiments, the gel compositions can be delivered to the surface of the scalp to promote hair growth. In some embodiments, the gel compositions can be used to deliver of nutrient supplements in high concentrations where vitamins are provided by the GRAS gelator and/or from entrapped vitamins.

In some embodiments, the self-assembled gel compositions can be used for protection of skin from sunburns and inflammation, and delivery of antioxidants—where antioxidant properties are provided by the GRAS gelator and/or from entrapped antioxidants. The gel compositions can be used in the treatment of back pain, carpal tunnel syndrome, diabetic retinopathy, ulcerative colitis, crohn's disease, tennis elbow, heart disease, cardiovascular disease, and peripheral vascular disease. The gel compositions can be useful, e.g., for improving safety, targeting efficiency, compliance and efficacy for indications benefiting from single dose, prolonged action or tissue-specific formulations. Exemplary indications include, but are not limited to, allergy (e.g. contact dermatitis), arthritis, asthma, cancer, cardiovascular disease, diabetic ulcers, eczema, infections, inflammation, muscuscitis, periodontal disease, psoriasis, respiratory pathway diseases (e.g., tuberculosis), vascular occlusion, pain, graft versus host diseases, canker sores, mucositis, bacterial conditions, viral conditions.

In some embodiments, the self-assembled gel compositions can include stimulation of pathways to promote formation of extracellular matrix (i.e. gel composition induces formation of collagen that may find utility in cosmetic applications, or promotes formulation of new tissues such as muscle or other connective tissues).

It is possible to administer the gel compositions through various known delivery techniques, including injection and implantation. Injection and implantation are particularly feasible in view of the ability of the gelator to form in situ (i.e. in situ self-assembly). Injecting or implanting the gel compositions into a joint together with the sustained-release properties enables the gel compositions to provide a long-term release of an encapsulated agent over a period of time. This is particularly suitable in instances where enzymes that are present in a joint are naturally released upon inflammation of the joint. When the joint becomes inflamed and releases the enzyme, the enzyme, in turn, disassembles gel compositions, which releases the anti-inflammatory drugs. After the anti-inflammatory drug is released, the enzyme concentration decreases. The gel compositions that are not cleaved remain stable until another inflammatory stimulus. This phenomenon can be referred to as "on-demand release," where the level of inflammation regulates the amount and timing of an agent release. In some embodiments, the gel compositions can be useful to release therapeutic agents that correlate with different stages of tissue regeneration.

Application may be through systemic infusion, injection, transplantation, inhalation, or topical application including to the mucosa, oral, buccal, nasal, intestinal, vaginal, rectal and skin. The gel compositions can be spatially targeted when administered to a biological system. For example, the gel compositions can be locally delivered via implants or injections, or the gel compositions can by systemically delivered. The active transfer of amphiphiles through a tissue can be enhanced/achieved by the action of electrical or other forms of energy. These may include iontophoresis; sonophoresis and electroporation. The gel compositions can be amenable to inner ear drug delivery, oral drug delivery, ophthalmologic application, and incorporation within chewing gum for controlled release of agents including flavoring agents, vitamins, or nutraceuticals. For example, the gel compositions can be in xerogel form and can be incorporated into a lozenge or chewing gum for controlled release of flavoring agents, vitamins, or nutraceuticals.

The self-assembled gel compositions can be used in transdermal delivery (e.g., transdermal patches, permeabilization), and combined with other external devices which can be applied on the skin. The gel compositions can be used for intranasal delivery of drugs, in various cosmetic applications including bulking agents or for applications where production of extracellular matrix such as collagen is desired. For example, the gel compositions can be in xerogel form and administered to an intranasal cavity by inhalation. In some embodiments, the gel compositions can be used for delivering drugs into the gut and inner-lumen of vessels through endoscopic application (endoluminal applications), which can offer advantage over trans dermal patches that can induce inflammation or cause skin irritation.

The self-assembled gel compositions can be used with Natural Orifice Transluminal Endoscopic Surgery ("NOTES") to localize drug delivery devices within or between specific internal tissues. In some embodiments, the gel compositions can be delivered to a tumor for sustained delivery of chemotherapeutics, or can be delivered to a site of healthy tissue following cancer resection to decrease the chances of recurrence. For example, gel compositions including a PARP inhibitor and a chemotherapeutic agent can be delivered by injection or by implantation at a brain cancer site for sustained anticancer therapy, by blocking one or more cellular repair mechanisms.

In some embodiments, the gelators can be applied to a biological system and self-assembly can occur in situ. For example, the gel compositions described herein may be applied to the surface of bone and the gel can be assembled within the pores of the bone. For example, heated gel compositions can be injected in solution form to a bone site, which can then cool to physiological temperatures to assemble into gel forms.

EXAMPLES

The invention is further described in the following examples, which do not limit the scope of the invention described in the claims.

Example 1

The gelation ability of vitamin precursors in combination with other vitamin precursors or GRAS agents has been investigated. Representative results are presented below.

TABLE 1-1

1:1 retinyl acetate (vitamin A precursor)
in ascorbyl palmitate (vitamin C precursor)

| Wt % retinyl acetate | Wt % ascorbyl palmitate | Solvent | Precipitation/ Gelation/ Soluble (P/G/S) |
|---|---|---|---|
| 6% | 6% | DMSO in water 70% | No gel |
| 6% | 6% | DMSO in water 30% | G |
| 6% | 6% | Ethanol in water 30% | G |
| 6% | 6% | DMF in water 30% | G |

TABLE 1-2

1:2 Retinyl Acetate (vitamin A precursor)
in Ascorbyl palmitate (vitamin C precursor)

| Wt % retinyl acetate | Wt % ascorbyl palmitate | Solvent | Precipitation/ Gelation/ Soluble (P/G/S) |
|---|---|---|---|
| 3% | 6% | DMSO in water 30% | G |
| 3% | 6% | Ethanol in water 30% | G |
| 3% | 6% | DMF in water 30% | G |

TABLE 1-3

1:1 Alpha-tocopherol Acetate (vitamin
E precursor) in Ascorbyl palmitate

| Wt % tocopherol acetate | Wt % ascorbyl palmitate | Solvent | Precipitation/ Gelation/ Soluble (P/G/S) |
|---|---|---|---|
| 4% | 4% | DMSO in water 30% | No gel |
| 4% | 4% | DMF in water 30% | G |
| 4% | 4% | Acetone in water 30% | G |
| 4% | 4% | Ethanol in water 30% | G |

TABLE 1-4

25:1 Alpha-tocopherol Acetate (vitamin E precursor)
in Ascorbyl palmitate (vitamin C precursor)

| Alpha tocopherol | Ascorbyl palmitate | Solvent | G/P/S |
|---|---|---|---|
| 0.2 g | 8 mg | DMSO - 80 μl | S |
|  |  | H$_2$O - 20 μl | Emulsion |
| 0.2 g | 8 mg | EtOH - 80 μl | S |
|  |  | H$_2$O - 20 μl | G |
| 0.2 g | 8 mg | CHCl$_3$ - 80 μl | G |
| 0.2 g | 8 mg | Toluene - 80 μl | S |

TABLE 1-5

Using Alpha tocopherol Acetate and
Retinyl Palmitate as the solvent

| GRAS gelator | Solvent/second non-independent gelator | Result |
|---|---|---|
| Ascorbyl palmitate | Alpha tocopherol acetate |  |
| 20 mg (9%) | 0.2 g | Insoluble |
| 20 mg (6.25%) | 0.3 g | Insoluble |
| Ascorbyl palmitate | Retinyl palmitate |  |
| 3 mg (1.5%) | 0.2 g | Precipitate |
| Sorbitan monostearate | Retinyl palmitate |  |
| 5 mg (2.5%) | 0.2 g | Soluble |
| 6 mg (3%) | 0.2 g | Soluble |
| Triglycerol monostearate | Alpha tocopherol acetate |  |
| 3 mg (1.5%) | 0.2 g | Soluble |
| 9 mg (4.5%) | 0.2 g | Gel |

Example 2

We have focused our attention on the development of enzyme-responsive self-assembled nano/microfibrous hydrogels that can easily be injected into the articular space, yet are much larger than free drug, which should increase residence time by preventing rapid clearance by the lymphatic system. The inherent nanometer-scale features of this self-assembled noncrosslinked hydrogel maximize the interaction with specific enzymes for rapid disassembly and drug release. Gels made from ascorbyl palmitate (Asc-Pal) can encapsulate model agents, withstand shear forces that may be experienced in dynamic environments such as joints, remain stable following injection into healthy joints of mice, and can disassemble in vitro to release encapsulated agents in response to synovial fluid from arthritic patients. A graphical representation of an agent encapsulation by a self-assembling gel, and the subsequent disassembly and agent release process is shown, for example, in FIG. 1.

Ascorbyl palmitate ("Asc-Pal") and matrix metalloproteinases were purchased from Sigma Aldrich (St. Louis, Mo.). The Novozyme 435 (lipase B from *Candida antarctica*) and Lipolase 1001 were obtained from Novozymes through Brenntag North America. 1, 10-Dioctadecyl-3,3,30,30-tetramethylindodicarbocyanine, chlorobenzenesulfonate salt (DiD) dye was purchased from Invitrogen.

Preparation of Gels

Typically, solvents (0.2 mL) were added to a glass scintillation vial with the gelator (0.5-5 wt/vol %) and sealed with a screw cap. The vial was heated to about 60-80° C. until the gelator was completely dissolved. The vial was placed on a stable surface and allowed to cool to room temperature. Typically after 15-45 min, the solution was transitioned into a viscous gel. Gelation was considered to have occurred when no gravitational flow was observed upon inversion of the glass vial, and resulted hydrogels are injectable. Asc-Pal formed gels in water, benzene, toluene, carbon tetrachloride, and acetonitrile; while a precipitate formed in dimethylformamide and dimethylsulfoxide. Asc-Pal was soluble in chloroform and methanol.

The morphologies of the self-assembled hydrogels were examined using SEM and fluorescence polarizable optical microscopy. Investigation of the hydrogels formed from Asc-Pal with SEM showed that hydrogels form fibrous structures with fiber thicknesses of 20-300 nm and fiber lengths of several microns. The anisotropic nature of intermolecular interactions between amphiphile molecules is supported by the high aspect ratios of the gel fibers. Dye-encapsulating fibers were rinsed with excess PBS to remove unencapsulated dye, and subsequent fluorescence microscope images of the fibers indicated that the dye was encapsulated within the fibers.

Enzyme-Responsive Fiber Disassembly and Release of Dye

We demonstrate the encapsulation of a model dye in Asc-Pal hydrogel, which upon enzyme-mediated gel degradation releases the encapsulated dye at model physiological conditions in a controlled manner. Specific enzymes are significantly upregulated within arthritic joints, and their expression and concentration correlate with the degree of synovial inflammation. Thus, we have tested the ability of self-assembled gel fibers to release an encapsulated payload in response to the enzymes that are expressed within arthritic joints.

DiD-encapsulating gel fibers were dispersed within PBS and incubated at 37"C with either lipase (esterase or MMP-2, or MMP-9 enzyme (100 ng/mL). At regular intervals, aliquots of samples were collected, and release of the dye was quantified using absorption spectroscopy. Plotting cumulative release of the dye (%) versus time (FIG. 2A) revealed that lipase and MMPs trigger fiber disassembly to release the encapsulated dye, whereas gels in PBS controls remained stable and did not release significant amounts of dye. Additionally, through thin-layer chromatography, we identified the presence of ascorbic acid and palmitic acid (confirmed by comparing Rf values by cospotting with authentic samples of ascorbic and palmitic acids) only in gel solutions that contained enzymes. We have shown that gels in PBS remain stable for at least 3 months, indicating that the presence of enzymes is required for gel disassembly and the release of encapsulated agents. This result confirms the absence of loosely bound dye on the surface of the gel fibers.

Figure 2A:
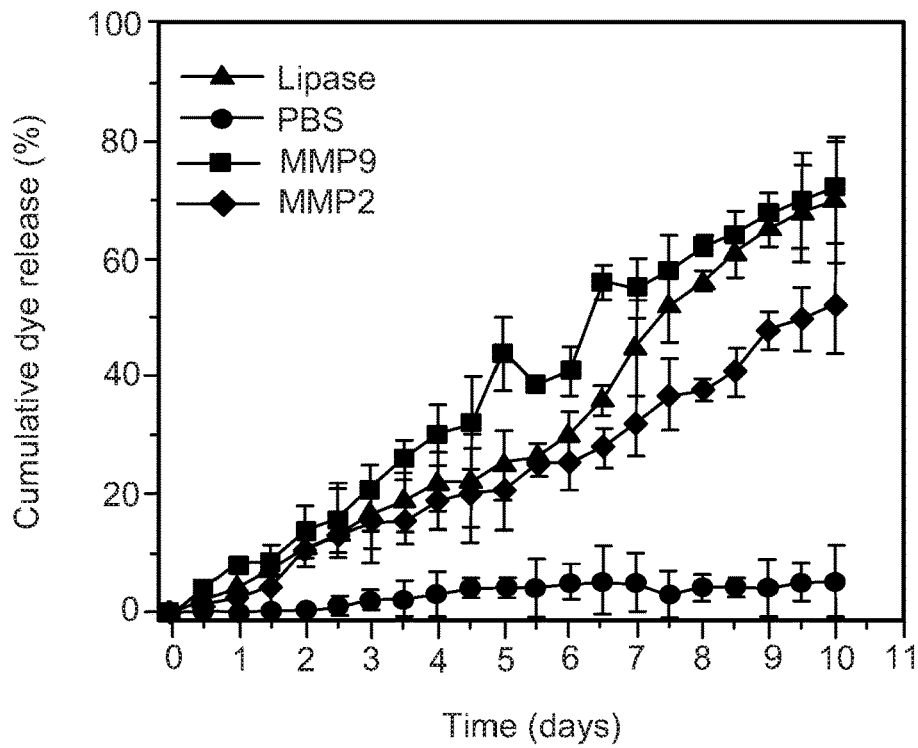
FIGS. 2A and 2B are graphs showing agent release from an ascorbic palmitate ("Asc-Pal") self-assembled gel fibers in response to lipase, MMP-2, and MMP-9 at 37° C. in vitro. (A) Enzyme was added on day 0, and release kinetics were continuously monitored. (B) After 4 days of enzyme addition, media were changed to remove the enzyme (dotted arrow); on day 11, fresh enzyme was added (solid arrow), triggering the release of dye.
Figure 2B:
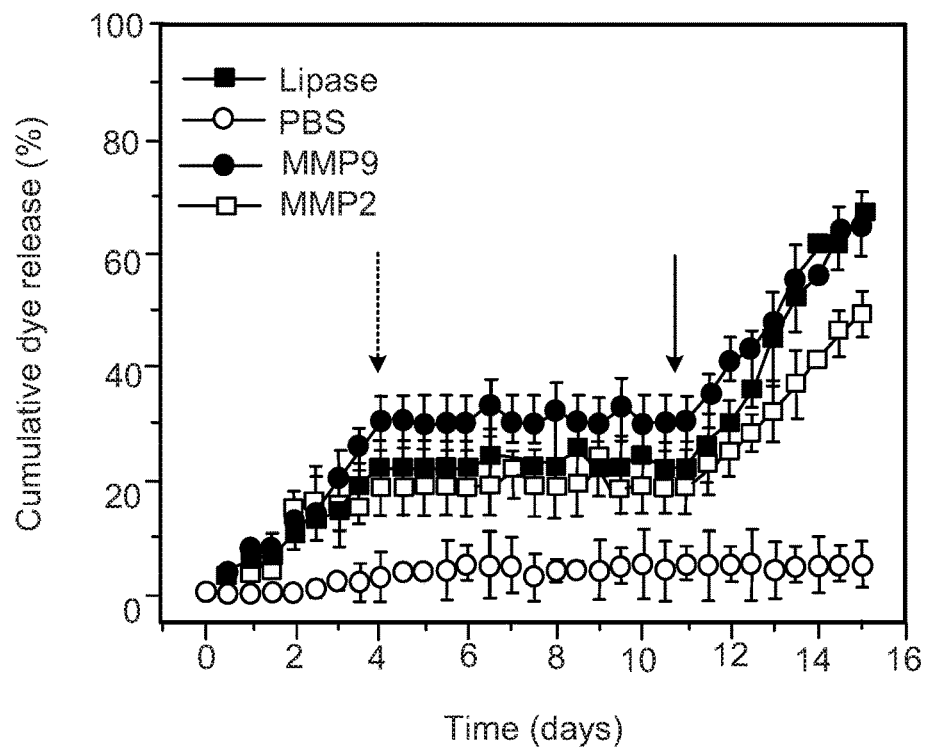

In the absence of enzymes, mechanical agitation of the fibers through rigorous vortexing did not induce the release of dye, indicating that agents incorporated within the fibers remain stably entrapped. Importantly, in the present system, we did not observe burst release (FIGS. 2A-2B). To investigate the potential for on-demand disassembly, following a 4-day incubation with enzyme (MMP-2, MMP-9, or lipase) containing media that triggered disassembly of fibers, media were replaced with PBS, which halted the disassembly of fibers and the release of dye. After a subsequent 7-day incubation with PBS, enzymes were added to the suspended fibers, triggering disassembly and the release of the encapsulated dye (FIG. 2B). These results clearly suggest that Asc-Pal self-assembled fibers respond to proteolytic enzymes that are present within arthritic joints and release encapsulated agents in an on-demand manner.

Arthritic Synovial Fluid Induces Fiber Disassembly

Figure 3A:
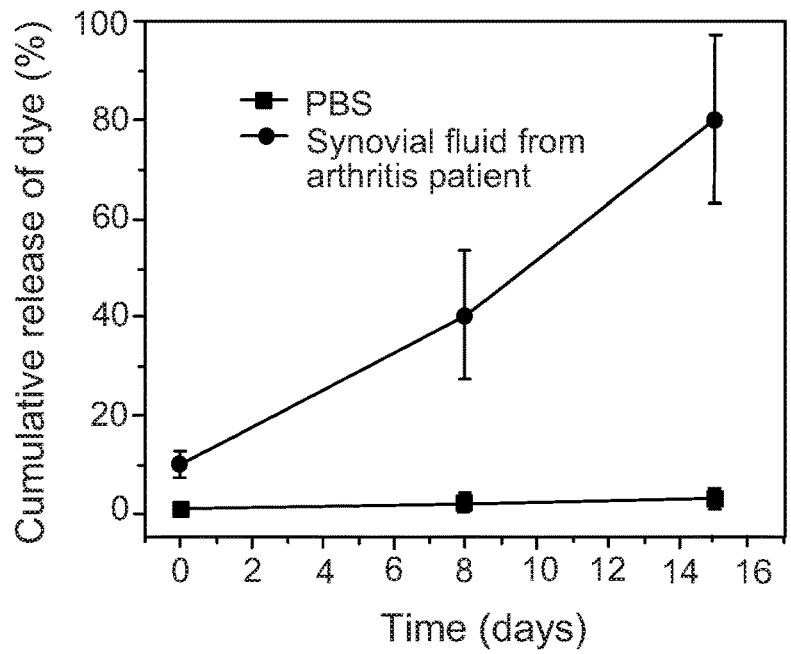
FIGS. 3A and 3B are graphs showing (A) synovial fluid collected from arthritis patients mediated fiber disassembly and dye release over a 15-day period, whereas dye was not released from gels incubated with PBS. (B) Gel fibers were incubated with synovial lysates prepared from ankle tissue of arthritic mice with and without protease inhibitors.

DiD-encapsulating fibers were incubated in arthritic synovial fluid at 37° C., and the release of dye was quantified over a period of 15 days. Plotting cumulative release of the dye (%) versus time (FIG. 3A) revealed that synovial fluid triggers fiber disassembly leading to the release of the dye.

Figure 3B:
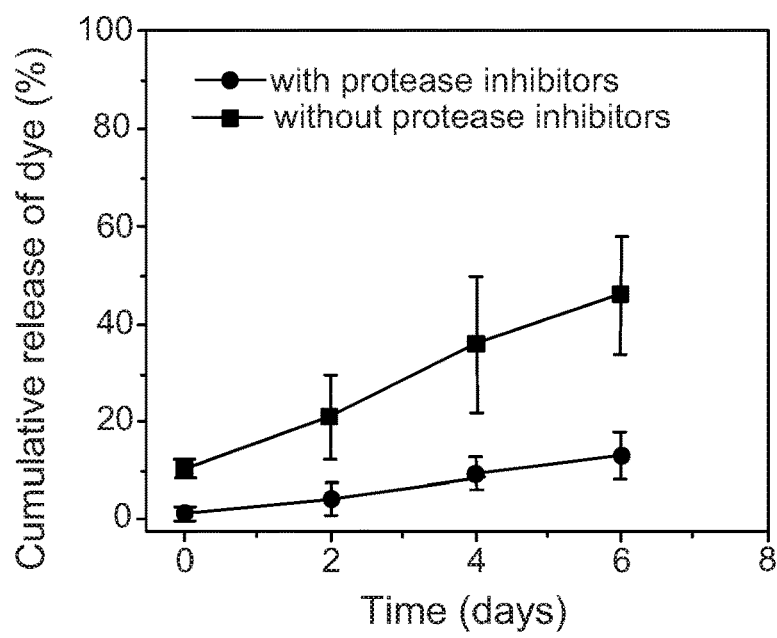

To determine whether proteases that are present in arthritic joints were responsible for fiber disassembly, we prepared lysates from arthritic joints of mice in the presence and absence of protease inhibitors. Incubation of self-assembled gel fibers with these lysates was used to help reveal the role of arthritis-associated proteases. The presence of protease inhibitors significantly reduced fiber disassembly and dye release, thus demonstrating that the presence of enzymes was critical for promoting the release of agents from gels formed from Asc-Pal (FIG. 3B.).

Fiber Stability in Joints Under Nonarthritic Conditions

To investigate the stability of fibers in the absence of inflammation, fibers were injected into the joints of healthy mice using a small-bore (27 gauge) needle. Eight weeks post-implantation, the ankles of mice were sectioned and imaged with optical and fluorescence microscopy to observe the presence of fibers. Images of tissue sections revealed that DiD-encapsulating fibers were present, suggesting the potential for long-term hydrolytic stability of the fibers in vivo.

Reversible Self-Assembly of Fibers

Materials that are injected into the joint space experience cyclical mechanical forces during ambulation; thus, it is important that materials that are injected into the joint can withstand these forces and retain their characteristic material properties such as mechanical strength and morphology.

Figure 4A:
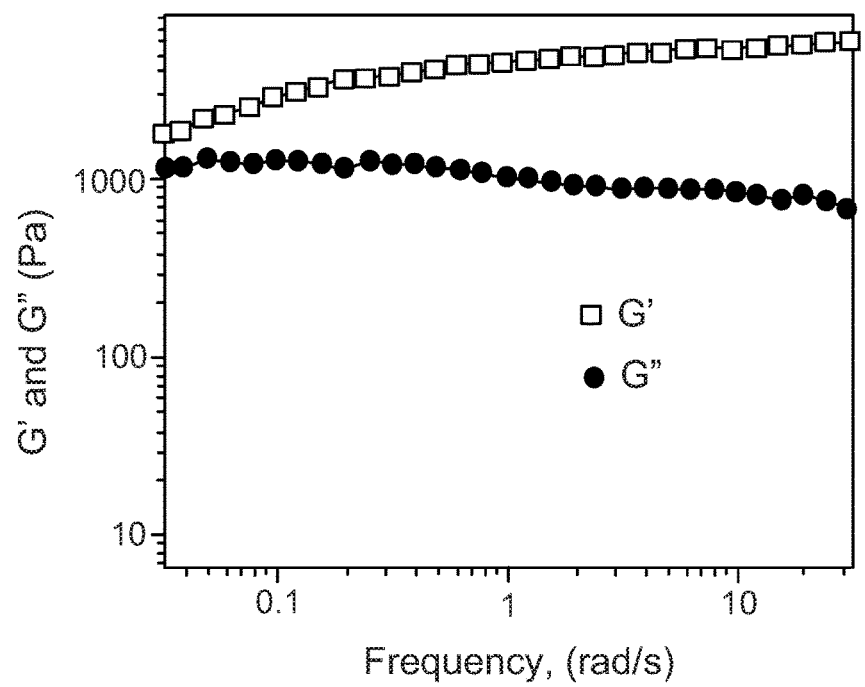
FIGS. 4A and 4B are graphs showing dynamic rheology of Asc-Pal fibrous hydrogels assessed with a parallel-plate rheometer. (A) Storage modulus, GO, and viscous modulus, G", over a frequency range of 0-12 rad/s; (B) Frequency sweeps conducted before/after multiple cycles of a high shear stress to measure GO.

To investigate the impact of relevant mechanical forces on the Asc-Pal fibers, we subjected gel nanofibers to cyclical shear forces and examined their resulting rheological properties using a rheometer equipped with a parallel-plate geometry (FIG. 4A). The elastic/storage modulus G' was independent of frequency and was much higher than the viscous modulus G" over the frequency range (0-12 rad/s) examined (FIG. 4A). This type of response is typical of gels, as it shows that the sample does not change its properties or "relax" over long time scales. The value of G' is a measure of the gel stiffness, and its value here (>1000 Pa) indicates a gel of slightly higher strength than collagen platelet gels. The mechanical properties and strength of these gels are comparable with earlier reported self assembled peptide gels that are being examined as possible injectable joint lubricants for the treatment of osteoarthritis.

Figure 4B:
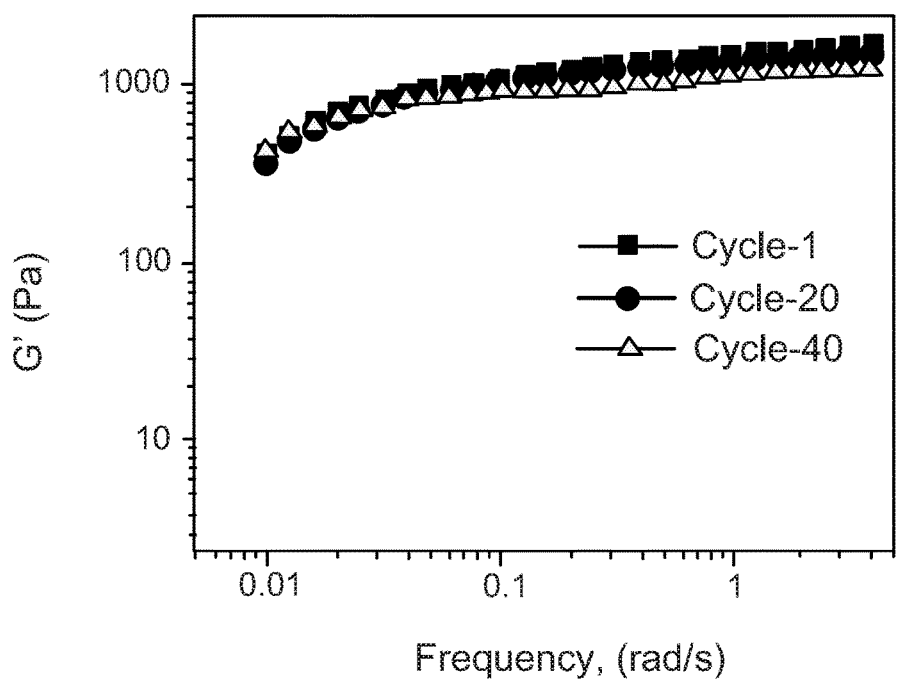

Frequency sweeps conducted before/after multiple cycles (1, 20, and 40) of a high shear stress were used to measure G' (storage modulus). Interestingly, no significant differences were observed after 40 cycles (FIG. 4B), indicating that the gel fibers retain their mechanical strength.

These results indicate that self-assembled fibers made of Asc-Pal have the potential to retain their morphology and mechanical properties even under the dynamic forces that may be experienced during ambulation.

Example 3

Figure 5:
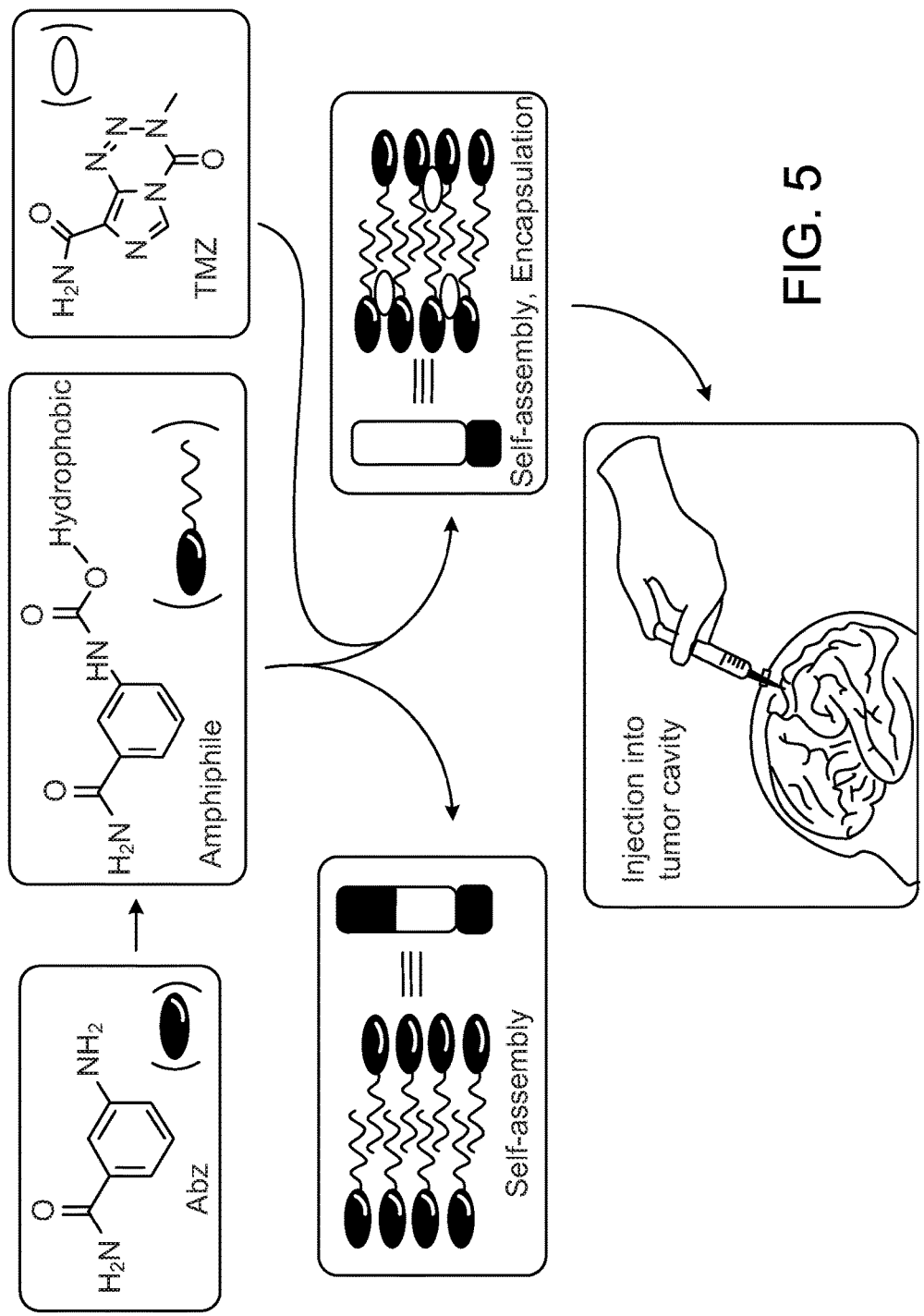
FIG. 5 is a graphical representation of a self-assembling gel including a 3-aminobenzamide derivative and optionally an encapsulated tomozolomide.

We set out to design an Abz-derived amphiphile that would encapsulate temozolomide, and release it only upon contact with enzymes closely associated with the presence of glioma cells, namely, the family of matrix metallopeptidases (MMPs) commonly found at sites of inflammation. By adding a hydrophobic group to the water-soluble Abz through a carbamate linkage, a hydrolytically stable, enzyme cleavable amphiphile could be synthesized (FIG. 5). This amphiphile could then be made to undergo self-assembly either alone or in the presence of temozolomide, in which case the chemotherapeutic agent would be encapsulated within the gel. Such a temozolomide-encapsulating Abz-derived gel would then be injected into the tumor cavity post-resection, providing an on-demand reservoir of chemotherapeutic agent in conjunction with free Abz, both to be released upon contact with glioma cells.

A variety of Abz-derived amphiphiles were synthesized (Scheme 3-1). Gelation conditions were explored for the set of amphiphiles, with the exception of Abz-PNP, which was found to decompose spontaneously. In general, mixtures of polar organic solvents with water gave the best gelation results, with only two pure organogels forming (Abz-Alloc in glycerol, and Abz-Chol in 1,4-dioxane). Solvent systems that were found to promote gelation were further explored with respect to concentration and ratio of solvents. The four amphiphiles had widely different solubility and gelation properties, with each amphiphile forming at least two gels.

Scheme 3-1. Structures of synthesized Abz-derived amphiphiles.

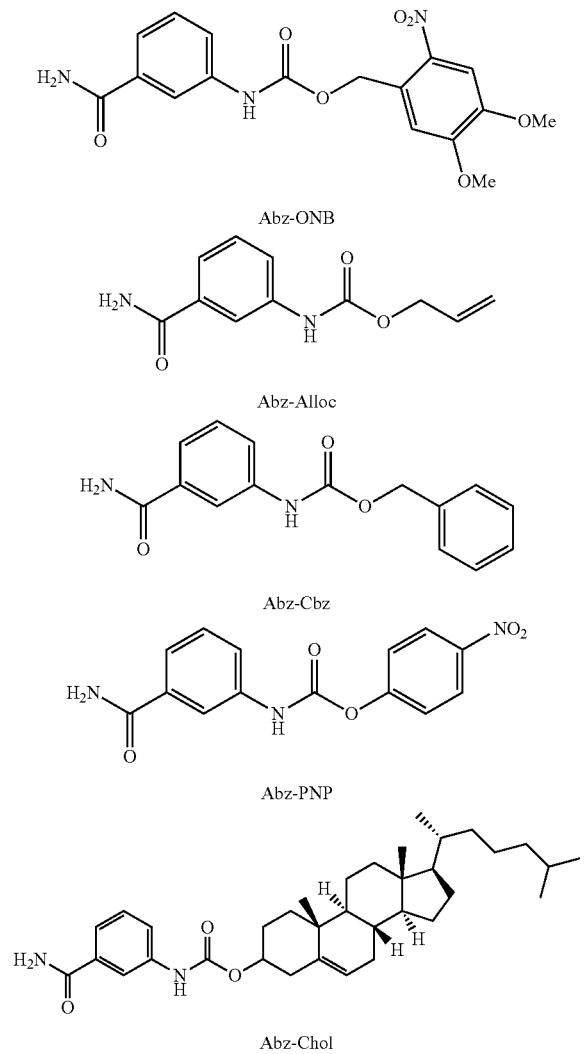

Gels formed from Abz-ONB and Abz-Chol both presented as fibrous structures under bright field microscopy, suggesting the formation of self-assembled fibers. Gels of Abz-Alloc and Abz-Cbz, however, did not reveal any fibers, and instead appeared highly crystalline in nature, suggesting that these amphiphiles were not forming fibrous gels.

We tested the encapsulation abilities of Abz-ONB and Abz-Chol by including curcumin in the organic solvent used for gelation. Such gels were washed with excess water and then observed under the FITC channel on the fluorescent microscope. The presence of curcumin could be observed in the gels of both Abz-ONB and Abz-Chol, and was located only within the fibers.

We next moved to testing the encapsulation of temozolomide. Abz-Chol successfully encapsulated temozolomide. We sought to use milder gelation conditions while allowing for flexibility in drug loading. Several methods were attempted, (a) adding the melted gel to solid temozolomide, (b) temozolomide wetted with the gelation solvent, and (c) temozolomide wetted with water. All three systems yielded nearly equivalent loading. We chose method (a) for continued use, and we hypothesized that avoiding contact between temozolomide and solvent for as long as possible would help to prevent degradation during formation. The weight-percent loading began to plateau at approximately 25%, which corresponds to a 1:1 mole ratio of temozolomide to Abz-Chol. A system including 6 mg of temozolomide in 12 mg of Abz-Chol was chosen for further investigation.

We characterized both the native Abz-Chol gel and the temozolomide-encapsulating gel through both bright field microscopy and scanning electron microscopy (SEM), and observed significantly different morphology. Under the light microscope, the native gel appeared semi-crystalline, while the encapsulating gel appeared as fluffy clumps. Under the electron microscope, the native gel appeared as large needles that upon further inspection were made from the tight association of micro and nano scale fibers. The encapsulating gel appeared as a highly fibrous interwoven network of micro and nano scale fibers, indicating that although the presence of temozolomide does not inhibit gelation, it does significantly change the ability of the formed fibers to aggregate into semi-crystalline bundles.

Figure 6:
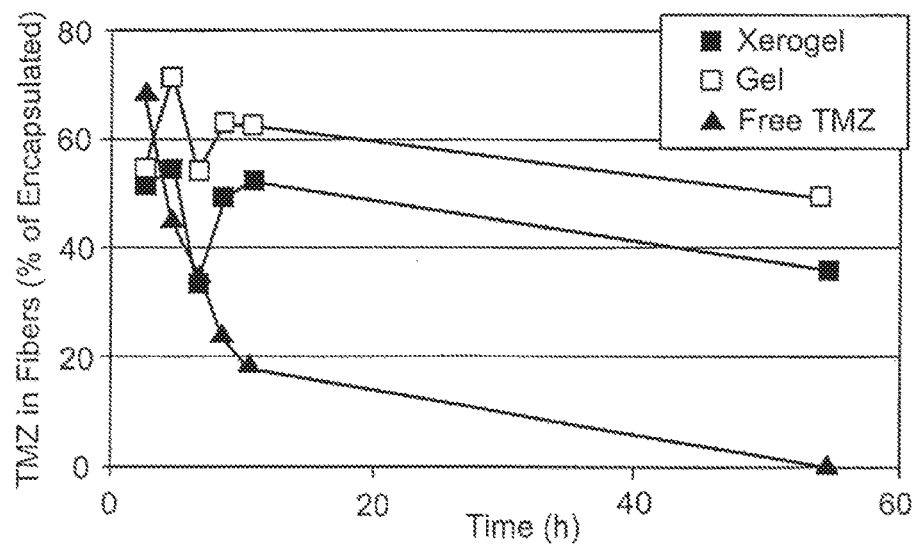
FIG. 6 is a graph showing increased stability of temozolomide (TMZ) in gel and xerogel formed from an Abz-Chol amphiphile.

We performed both stability and release studies on gels dispersed in the appropriate media (hereafter referred to as gel), and lyophilized gels dispersed in the appropriate media (hereafter referred to as xerogel). We first investigated the stability of temozolomide in fibers dispersed in DPBS over the course of two days compared to a control of free temozolomide in DPBS solution (FIG. 6). We achieved this by dissolving aliquots of fibers in DMSO at specified time points and measuring the temozolomide concentration inside by HPLC (Atlantis column). The data suggest that temozolomide is protected from hydrolysis, and degrades at a significantly slower rate both in gel and xerogel than free temozolomide. This is a very important indication, as an on-demand drug delivery depot would need to stabilize the rapidly hydrolyzed temozolomide until it is delivered.

Figure 7A:
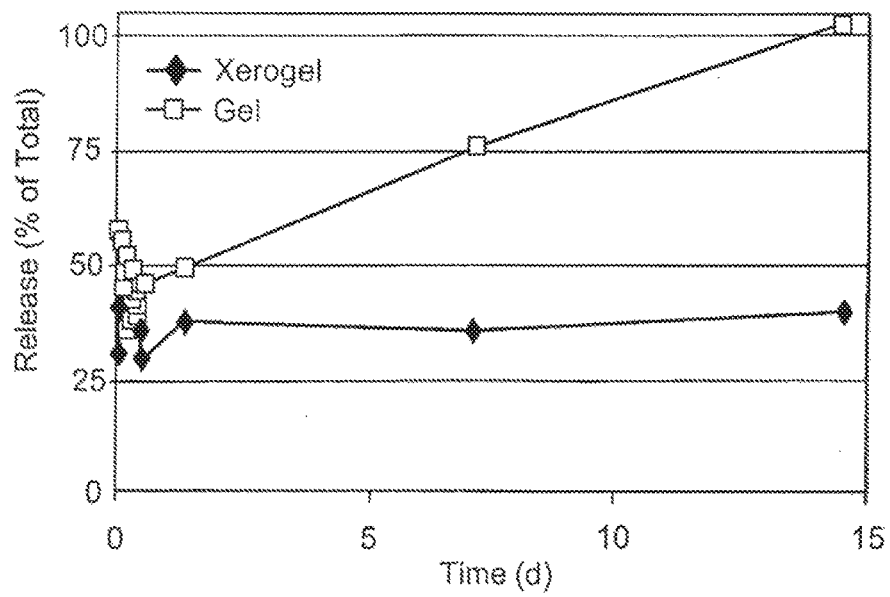
FIG. 7A is a graph showing a release of tomozolomide from gel fibers and xerogel fibers into DPBS at 37° C.
Figure 7B:
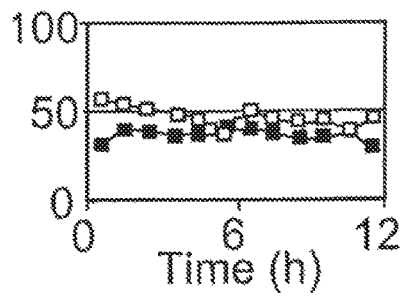
FIG. 7B is a graph showing arelease over first 12 hours.

We took unwashed gel and xerogel containing temozolomide, dispersed the fibers in DPBS, and followed the supernatant concentration of temozolomide and AIC over the course of two weeks by HPLC (Atlantis column). In both formulations we observed an expected initial burst associated with the nonencapsulated temozolomide (FIG. 7); however, this was much greater in the case of the gel (57% vs. 31% for xerogel). Both formulations were relatively stable over the first day; however, over the course of the experiment the gel continued to release temozolomide, eventually releasing the full load, while the xerogel did not release beyond the expected burst.

Figure 8:
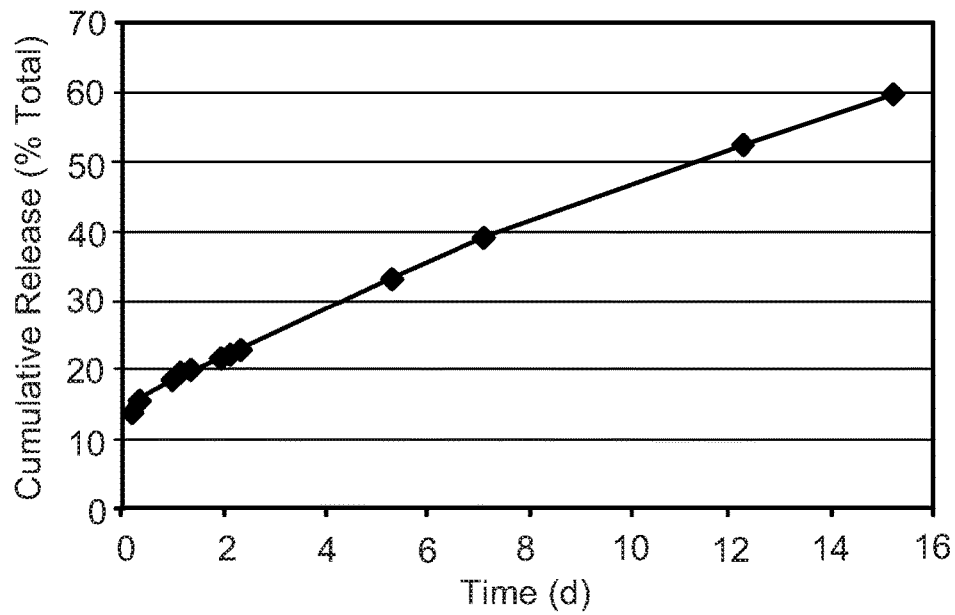
FIG. 8 is a graph showing a cumulative release of tomozolomide in DPBS at 37° C. from a transwell formulation, measured by high performance liquid chromatograph ("HPLC").

We also evaluated the ex vitro release profile of the transwell-based xerogel formulation. Transwells containing the air-dried in situ formed xerogels were incubated in DPBS in triplicate. At each time point the media was removed, the volume measured, and the composition measured by HPLC, replacing with fresh media. In this manner cumulative release was measured over the course of two weeks, the results of which are presented in FIG. 8. We observed a significantly smaller burst release compared with previous release studies, followed by a steady release of temozolomide, reaching approximately 60% after 15 days. The lower burst release was likely the result of less agitation in the context of a cell culture plate.

In order to further understand the mechanism of temozolomide encapsulation, and to probe the effects of enzyme-catalyzed degradation, we synthesized two additional Abz-derived amphiphiles (Scheme 3-2). Structures were chosen to be as similar as possible with the exception of one being a carbamate and the other an amide.

Scheme 3-2. Structure of carbamate (Abz-O-10) and amide (ABZ-C-11) linked long chain amphiphiles.

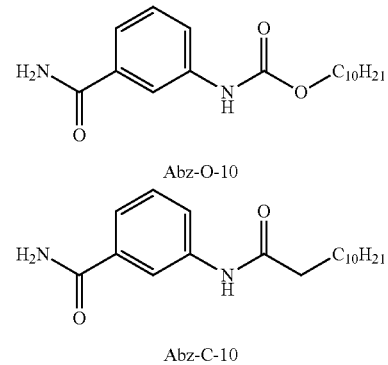

Abz-O-10

Abz-C-10

In sum, we have developed a series of novel 3-aminobenzamide-derived amphiphiles, which can be made to self-assemble in a variety of organic and aqueous solvent systems to form micro and nano fibrous structures. Under appropriate conditions, such gels were shown to encapsulate either curcumin or temozolomide, without disrupting self-assembly. Encapsulated temozolomide was stabilized against hydrolysis within the gel fibers, and the results of several release studies showed controlled release of drug under physiological conditions from several formulations. Such a system has broad applicability in the development of new delivery systems for several forms of brain cancer. Additionally, a new system was developed to allow for the delivery of hydrophobic xerogels to cells in culture through the use of transwell inserts, which can be used in future cell-based assays.

Materials and Methods

Synthesis

Abz-ONB:

To a solution of 3-aminobenzamide (223 mg, 1.6 mmol) in 1/1 1,4-dioxane/10% AcOH(aq) (26 mL total) was added 4,5-Dimethoxy-2-nitrobenzyl chloroformate (475 mg, 1.72 mmol) with stirring at r.t., producing a yellow suspension. After 23 hours the suspension was filtered through qualitative filter paper, washing with water. The collected yellow solid was dried in vacuo to give Abz-ONB (553 mg, 1.47 mmol, 90% yield). NMR in CDCl$_3$ with CD$_3$OD (500 MHz).

Abz-Alloc:

To a solution of 3-aminobenzamide (681 mg, 5 mmol) in 1/1 1,4-dioxane/10% AcOH(aq) (80 mL total) was added allyl chloroformate (0.56 mL, 5.25 mmol) with stirring at r.t. After 17 hours the clear solution was basified to pH 10 with 2 M NaOH(aq) and diluted with 60 mL of water to form a cloudy suspension that was stirred at r.t. for 2 hours. The mixture was diluted to a total volume of 250 mL with water and filtered through qualitative filter paper and dried in vacuo to give Abz-Alloc as an off-white solid (284 mg, 1.3 mmol, 26% yield). NMR in CDCl$_3$ with CD$_3$OD (300 MHz).

Abz-Chol:

To a flask containing 3-aminobenzamide (1.36 g, 10 mmol) and cholesterol chloroformate (4.72 g, 10.5 mmol) were added 1,4-dioxane (160 mL) and glacial acetic acid (8 mL) with vigorous stirring, generating a milky suspension that turned pale pink. The reaction was stirred at r.t. for 23 hours, at which point the suspension was basified to pH 10 with 2 M NaOH(aq), and diluted to a total volume of 600 mL with H$_2$O. The resultant off-white suspension was filtered through qualitative paper, washing with water to give a white solid and a yellow filtrate. The dried solid was washed with hexanes at 100 mg/mL 8 times, centrifuging to remove wash solvent. The resultant solvent was dried in vacuo to give Abz-Chol as a white solid (2.88 g, 5.2 mmol, 52% yield). NMR in DMSO-d6 (500 MHz).

Abz-Cbz:

To a solution of 3-aminobenzamide (681 mg, 5 mmol) in 1/1 1,4-dioxane/10% AcOH(aq) (80 mL total) was added benzyl chloroformate (745 µL, 5.25 mmol) in one portion with stirring. The resultant pale yellow solution was stirred at r.t. overnight, at which point it was basified to pH 11 with 2 M NaOH(aq), resulting in the formation of an off-white precipitate. The suspension was filtered through qualitative paper, washing with water and drying on filter to give Abz-Cbz (1.08 g, 4.0 mmol, 80% yield). NMR in CDCl$_3$ with CD$_3$OD (300 MHz).

Abz-O-10:

To a solution of 3-aminobenzamide (1.36 g, 10 mmol) in 1,4-dioxane (20 mL) and 10% AcOH(aq) (140 mL) was added decyl chloroformate (2.42 mL, 10.5 mmol) in one portion with stirring. The resultant cloudy emulsion was stirred at r.t. for 4 days, at which point the resultant orange suspension was basified to pH 10 with 2 M NaOH(aq), and filtered through qualitative paper, washing with water. The collected solid was dried in vacuo to give Abz-O-10 as a tan solid. NMR in DMSO-d6 (500 MHz).

Abz-C-11.

To a solution of 3-aminobenzamide (681 mg, 5 mmol) in 1,4-dioxane (20 mL) and 10% AcOH(aq) (60 mL) was added dodecanoyl chloride (1.21 mL, 5.25 mmol) in one portion with stirring. The resultant off-white suspension was stirred at r.t. for 3 days, at which point the suspension was basified to pH 9 with 2 M NaOH and filtered through qualitative paper, washing with water. The collected solid was dried in vacuo to give Abz-C-11 as a white solid. NMR in DMSO-d6 (500 MHz).

Gelation.

To a vial containing solid amphiphile was added the appropriate solvent. The vial was sealed and heated over a heat gun (~110° C. max) until amphiphile fully dissolved. The vial was allowed to cool undisturbed at room temperature, during which time gel formed. For all characterization gels were allowed to form for at least 45 minutes.

Encapsulation of Curcumin in Abz-Chol.

To a vial containing Abz-Chol (6 mg) was added curcumin in 1,4-dioxane (90 µL of 10 mg/mL). The vial was sealed and heated until full dissolution, at which point H$_2$O (10 µL) was added, causing gelation. The vial was again heated to full dissolution and allowed to cool, forming a yellow gel. The gel was mechanically broken and washed with H$_2$O (Millipore, 3×1 mL), centrifuging to remove washings. The resultant fibers were observed under bright field and fluorescence microscopy.

Encapsulation Efficiency and Loading.

To each vial containing Abz-Chol (12 mg) were added 1,4-dioxane (180 µL) and H$_2$O (20 Each vial was sealed and heated until full dissolution, and allowed to gel for a minimum of 1 hour. The gels were again heated to melting, quickly transferred to vials containing temozolomide (1, 3, 6, or 12 mg; each in triplicate), and allowed to gel for a minimum of 1 hour. Each gel was broken with pH 5 H$_3$PO$_4$(aq) (200 µL), and transferred to a 1.5 mL Eppendorf tube with pH 5 H$_3$PO$_4$(aq) (2×400 µL). The suspension was vortexed, centrifuged, and the supernatant removed. Fibers were washed with pH 5 H$_3$PO$_4$(aq) (1×1 mL), centrifuging to remove supernatant, and the composition of the combined supernatants was determined by HPLC (pondapak) after passing through a 0.2 µm Nylon or PTFE syringe filter.

Release and Stability

Preparation of all Gels.

To a vial containing Abz-Chol (12 mg) were added 1,4-dioxane (180 µL) and H$_2$O (20 µL). The vial was sealed and heated until full dissolution, and allowed to gel for a minimum of 1 hour. The gel was again heated to melting, quickly transferred to a vial containing temozolomide (6 mg), and allowed to gel for a minimum of 1 hour. Gels were then used as-is (gel), or frozen at −80° C. for a minimum of 30 minutes and lyophilized overnight (xerogel).

Release in DPBS.

6% wt/vol xerogels made on 200 µL scale, with 6 mg temozolomide loaded into each. Vials containing full xerogels were each placed in 20 mL scintillation vials, and DPBS (18.0 mL) was added, completely filling the inner vial. Larger vials were sealed and vortexed until xerogels were uniformly dispersed, and then stored in 37° C. incubator. At each time point vials were vortexed and 100 µL of suspension was removed, diluted 10×, and measured by HPLC (pondapak) following filtration through 0.2 µm Nylon syringe filter. Removed volume (100 µL) from vials was replaced at end of each time point.

Transwell Experiments

Transwell Insert for Cell Assay.

Three sets of gels were formed, loading 6 mg, 3 mg, and 1 mg of temozolomide in 12 mg of Abz-Chol. In each case, gels were melted and added to vials containing the appropriate amount of temozolomide. The vials were shaken briefly and immediately 2 µL of the resultant suspension was pipetted to the membrane of a transwell insert. Additionally, a control was prepared of Abz-Chol gel with no temozolomide. Each was performed in quadruplet. Transwell inserts were air dried for 1 week prior to use in cell culture.

Transwell Release.

To a vial containing Abz-Chol (12 mg) were added 1,4-dioxane (180 µL) and H$_2$O (20 µL). The vial was sealed and heated until full dissolution, and allowed to gel for a minimum of 1 hour. The gel was again heated to melting, quickly transferred to a vial containing temozolomide (6 mg), shaken to mix, and 4 µL aliquots added to the membrane of each of 6 24-well transwell inserts. Gels were allowed to dry open for 30 minutes, and then covered for 2 days. Inserts were added to 24-well plate and kept under DPBS or Lipolase (100 U/mL diluted 10× in DPBS) (1.5 mL initially, 1.0 mL for subsequent time points) in 37° C. cell culture incubator, each in triplicate. At each time point media was removed and replaced with fresh media of the same variety. The volume of the removed media was measured, and the composition measured by HPLC (pondapak)

following filtration through 0.2 μM Nylon or PTFE syringe filter. Cumulative release was thus calculated.

Example 4

Camptothecin was encapsulated in a PARP inhibitor. Camptothecin is a cytotoxic alkaloid which inhibits the DNA enzyme topoisomerase. DNA topoisomerase helps in relieving the torsional strain in the DNA during replication. Camptothecin binds to the topoisomerase 1 nicked DNA complex and prevents relegation. Since the DNA is damaged the cell undergoes apoptosis. However the cells have an inherent mechanism to rectify the process. An enzyme known as PARP gets activated when the DNA strand is broken and recruits DNA repairing enzyme and repairs the broken DNA. Camptothecin is sparingly soluble in water, easily convertible to inactive carboxylate form and undesirable systemic side effects. Hence an effective method for treatment of glioblastomas would be to co-encapsulate both Camptothecin and PARP inhibitor and release the drug in a sustained manner for a long period of time.

We have investigated the self-assembled ability of sorbitan monostearate (SMS, GRAS-agent, Scheme 4-1) in a wide range of solvents, minimum gelation concentrations in various solvents, and their morphology using electron microscope. In addition, we have also investigated the ability of SMS gels to encapsulate a chemotherapeutic agent, camptothecin (CPT) and different PARP-inhibitors. Encapsulation efficiency, loading capacity, stability of gels and detailed release kinetics in response to the enzymes have been investigated. Detailed results have been summarized in following sections.

Scheme 4-1. Chemical structure of sorbitan monostearate (SMS).

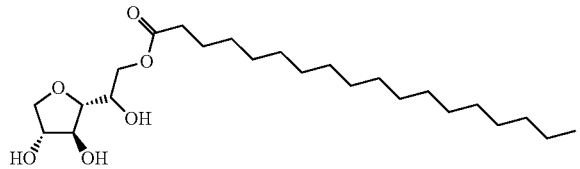

Results
Gelation Ability of SMS.

Table 4-1 shows the versatile self-assembling ability of SMS in various solvents. Intriguingly, SMS has demonstrated appreciable ability to self-assemble in aqueous solution and also in polar aprotic (dimethyl sulfoxide, dimethyl formamide) and protic solvents (ethylene glycol, polyethylene glycol) as well as non-polar solvents like isopropyl palmitate, hexanes and hexadecane (Table 4-1). These results clearly indicate the versatile gelation ability of SMS amphiphile.

TABLE 4-1

Gelation ability of amphiphile SMS in a wide range of solvents.

| Solvent | Sorbitane Monostearate |
| --- | --- |
| Water | Gel |
| Dimethyl sulfoxide (DMSO) | Gel |
| Dimethyl formamide (DMF) | Soluble |
| Acetone | Precipitate |
| Acetonitrile (CH$_3$CN) | Precipitate |
| Methanol | Precipitate |
| Ethanol | Soluble |

TABLE 4-1-continued

Gelation ability of amphiphile SMS in a wide range of solvents.

| Solvent | Sorbitane Monostearate |
| --- | --- |
| Isopropanol | Soluble |
| Isobutanol | Soluble |
| Glycerol | Gel |
| Mono-ethylene glycol | Weak Gel |
| Polyethylene glycol dimethyl acrylate | Increased Viscosity |
| Dioxane | Soluble |
| Tetrahydrofuran (THF) | Soluble |
| Isopropyl palmitate | Clear Gel |
| Ethyl acetate | Emulsion |
| Chloroform | Soluble |
| n-hexane | Gel |
| n-hexadecane | Gel |
| Toluene | Soluble |
| Xylene | Soluble |
| Tetrachloro methane | Soluble |

Concentration was around 5-9%

In addition, SMS has demonstrated different minimum gelation concentrations (MGC) in different solvents (Table 4-2). MGC values of SMS have varied from 3 to 8 wt/v %.

TABLE 4-2

Minimum gelation concentration of amphiphile SMS in gelling solvents.

| Solvent | Sorbitane Monostearate | Minimum Gelation Concentration (Wt/V %) |
| --- | --- | --- |
| Water | Gel | 3% |
| Dimethyl sulfoxide (DMSO) | Gel | 3% |
| Ethylene glycol | Gel | 5% |
| Glycerol | Gel | 8% |
| Isopropyl palmitate | Gel | 3% |
| n-hexane | Gel | 4% |
| n-hexadecane | Gel | 2% |

Encapsulation of Camptothecin.

Chemotherapeutic agent camptothecin (CPT) is a hydrophobic drug, which has very low water solubility. Thus, we investigated the encapsulation ability in SMS gels. Results are summarized in Table 4-3. Interestingly, SMS gels have shown high loading ability, i.e., 4 and 6% (wt/v) SMS gels were shown ~30% (wt/wt) loading efficacy (Table 4-3).

TABLE 4-3

Camptothecin loading efficiency of self-assembled gels of SMS in DMSO

| Sorbitane Monostearate, % (wt/v) | Camptothecin starting concentration (mg) | Loading efficiency % (wt/wt) |
| --- | --- | --- |
| 4 | 4 | 32.28 |
| 6 | 4 | 30.02 |
| 8 | 4 | 18.25 |
| 12 | 4 | 12.67 |

Morphology of Self-Assembled Gels of SMS.

We have characterized the morphology of self-assembled gels of SMS in their native gel form as well as CPT encapsulated gels. DMSO gels of SMS and CPT-encapsulated gels both show similar morphology under scanning electron microscopy.

Similarly, we have characterized the morphology of hydrogels (20% (v/v) DMSO in water) of CPT encapsulated SMS gels. Interestingly, at different weight percent of SMS (e.g., 4%, 8% and 12% (wt/v)) these gels showed only moderate differences in their morphology.

Controlled Release of Chemotherapeutic Agent.

Figure 9:
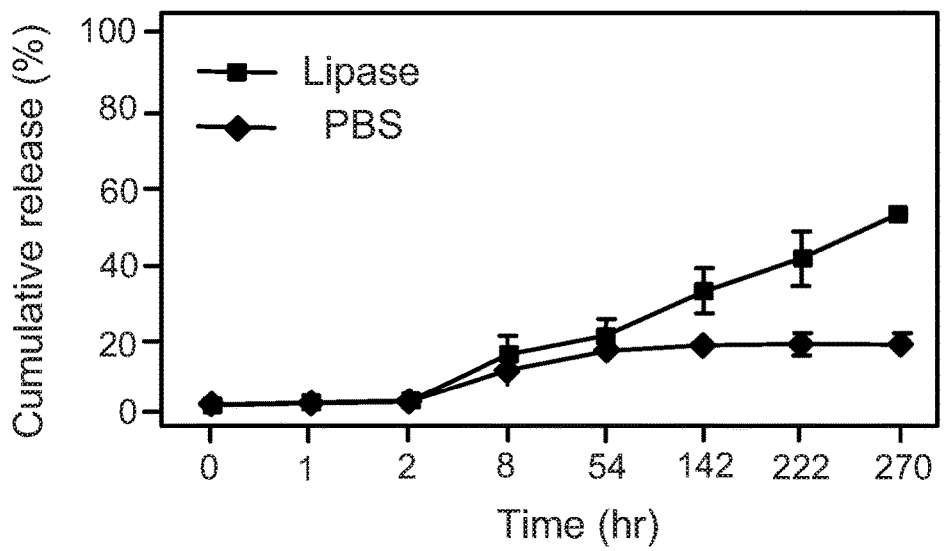
FIG. 9 is a graph showing controlled release of camptothecin from self-assembled hydrogel fibers of SMS (6%, wt/v) in the absence and presence of esterase enzyme (10,000 units) at 37° C.

Often drug delivery vehicles suffer from burst release and continuous release of cargo due to degradation of vehicles. Chemotherapeutic agent camptothecin (CPT) has been encapsulated in SMS gels with higher loading efficiency (30% (wt/wt)). Release kinetic experiments reveal that CPT encapsulated SMS gels do not have burst release (FIG. 9). In the absence of enzymes, these gels were stable and showed only moderate release of CPT (~15%) and reached plateau in ~8-10 hr. On contrary, in the presence of an esterase enzyme (lipase, 10,000 units) has showed enzyme-responsive release of CPT, which suggests that esterase enzyme can degrade the SMS gels in an on-demand manner to release the encapsulated drugs in a controlled manner (FIG. 9).

Cytotoxicity Studies of CPT Encapsulated SMS Self-Assembled Fibers.

Figure 10B:
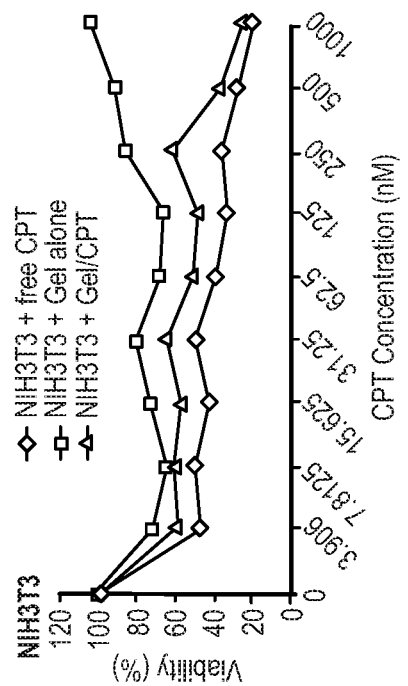
FIGS. 10A and 10B are graphs showing viability of (A) glioma cells (G55) and (B) fibroblasts (NIH3T3) in the presence of camptothecin-encapsulated self-assembled SMS gel fibers.
Figure 10A:
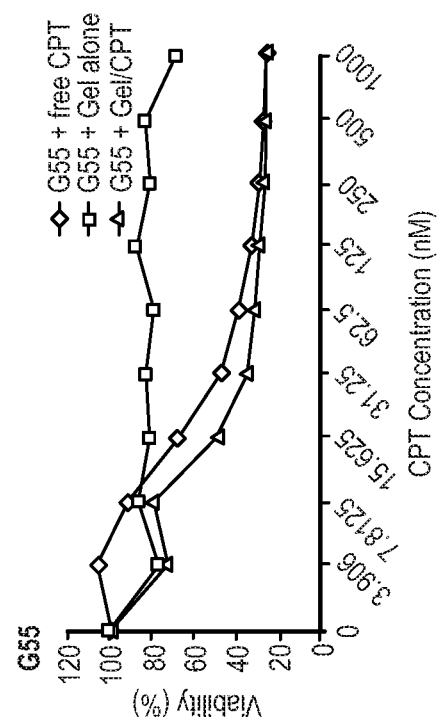

Prior to in vivo studies, evaluation of efficacy of drug delivery systems using appropriate cell lines is an essential step. Efficacy of CPT loaded SMS self-assembled fibers were investigated using glioma cell line, G55 and control cell line fibroblast, NIH3T3. When CPT-loaded SMS self-assembled fibers incubated in culture with G55 cells, the $IC_{50}$ of CPT-loaded SMS fibers was 15 nM, compared to 30 nM for CPT alone (FIG. 10A). On contrary, when CPT-loaded SMS self-assembled fibers incubated in culture with fibroblasts (NIH3T3), the $IC_{50}$ of CPT-loaded SMS fibers was 62.5 nM, compared to 3.9 for CPT alone (FIG. 10B). Intriguingly, CPT-loaded SMS fibers decreased 2-fold of $IC_{50}$ for gliomas G55, whereas CPT-loaded SMS fibers increased 15-fold of $IC_{50}$ for fibroblasts. We hypothesize that highly proliferative glioma G55 cells secretes high concentrations of enzymes that degrade the self-assembled fibers to release CPT efficiently, whereas free form of CPT degrades in the media due to its low half-life at physiological conditions. On contrary, fibroblast could not degrade the fibers to release CPT, thus $IC_{50}$ of encapsulated CPT (protected from hydrolytic degradation) has increased $IC_{50}$ (~15-fold). These results indicate that proliferative glioma cells triggers the drug release in an on-demand manner.

Encapsulation of Camptothecin and PARP-Inhibitor (AGO14699).

Chemotherapeutic agent camptothecin (CPT) is a hydrophobic drug, and PARP-inhibitor AGO14699 has moderate water solubility. Thus, both agents were encapsulated in hydrogel fibers of SMS to evaluate their synergistic efficacy against glioblastoma (brain cancer) cell lines. Inherent gelation ability of SMS did not altered in the presence of CPT and AGO14699; gelation results are summarized in Table 4-4. CPT and AGO14699 have been efficiently loaded in SMS hydrogel fibers with ~30 and 15% (wt/wt), respectively (Table 4-5).

TABLE 4-4

Gelation ability of sorbitan monostearate in the presence of camptothecin (CPT) and PARP-inhibitor (AGO-14699).

| Solvent | Sorbitane Monostearate + Camptothecin + PARP inhibitor |
|---|---|
| Water | Gel |
| Dimethyl sulfoxide (DMSO) | Gel |
| Isopropyl palmitate | Gel |
| Ethanol | Soluble |
| Isopropanol | Soluble |

TABLE 4-4-continued

Gelation ability of sorbitan monostearate in the presence of camptothecin (CPT) and PARP-inhibitor (AGO-14699).

| Solvent | Sorbitane Monostearate + Camptothecin + PARP inhibitor |
|---|---|
| Isobutanol | Soluble |
| Ethylene glycol | Gel |
| Polyethylene glycol | Weak Gel |
| Polyethylene glycol dimethyl acrylate | Increased Viscosity |

TABLE 4-5

Loading efficiency of camptothecin (CPT) and PARP-inhibitor (AGO-14699) in sorbitan monostearate DMSO gels.

Loading efficiency % (wt/wt)

| PARP-inhibitor (AGO14699), | Camptothecin (CPT) |
|---|---|
| 15.10 | 30.02 |

Figures 11A, 11B:
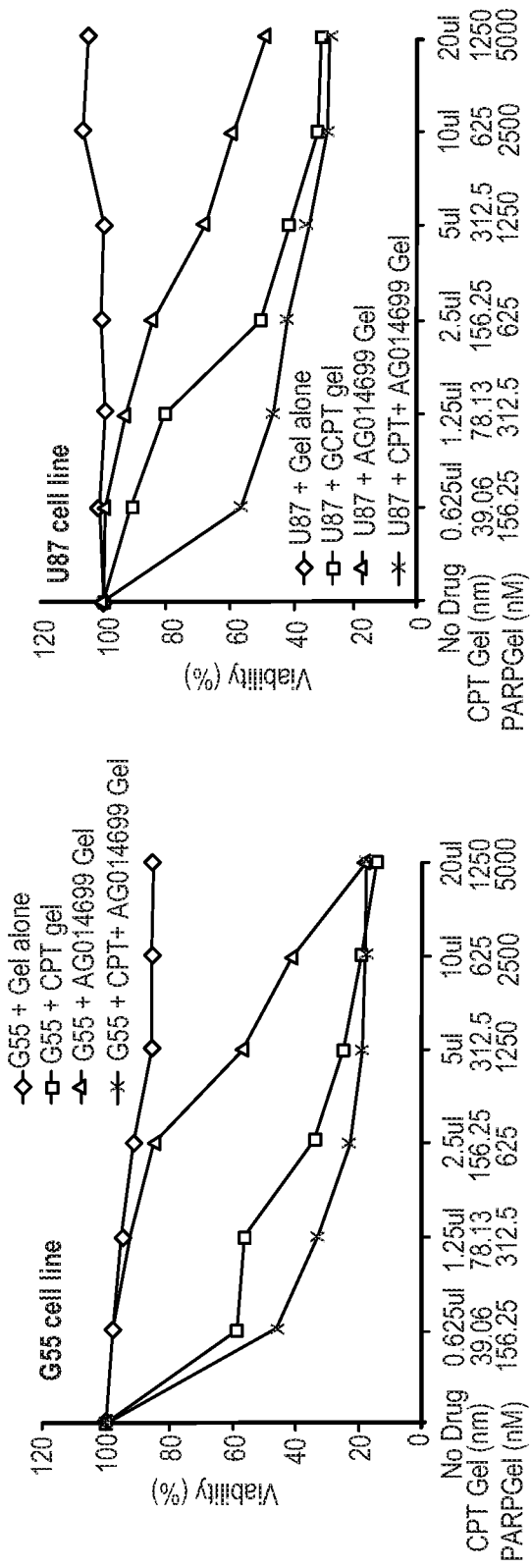
FIGS. 11A and 11B are graphs summarizing cytotoxicity of glioblastoma cancer cell lines ((A) G55 and (B) U87) using chemotherapeutic agent (CPT) and PARP-inhibitor (AGO14699) loaded Sorbitan Monostearate gels, individual and combination.

Cytotoxicity Studies of CPT and AGO14699 (PARP-Inhibitor) Encapsulated SMS Self-Assembled Hydrogels Efficacy of CPT and PARP-inhibitor loaded SMS self-assembled hydrogels were investigated using glioma cell lines G55 and U87. When CPT-PARP inhibitor loaded SMS hydrogels incubated in culture with G55 cells, the $IC_{50}$ of CPT-loaded and PARP-inhibitor loaded SMS gels were 105 nM and 1875 nM, compared to 36 nM for combination gel alone (FIG. 11A). Thus, 3-fold enhanced efficacy of chemotherapeutic agent, CPT has been observed with co-local delivery of CPT and PARP-inhibitor through self-assembled hydrogels. Interestingly, similar trend has been observed against U87 glioma cell line as well (FIG. 11B).

In summary, the SMS amphiphile has demonstrated an unprecedented ability to form self-assembled gels in a wide range of solvents including polar, non-polar, protic and aprotic solvents. SMS gels can encapsulate CPT with high loading efficiency, and stabilize the CPT to protect it from hydrolytic degradation. CPT-loaded SMS fibers can release CPT in the presence of ester enzymes in an on-demand manner. Cytotoxicity studies are in agreement with in vitro release studies, CPT-loaded SMS self-assembled fibers are very effective against glioma cells G55.

Example 5

We have also investigated the ability of SMS gels to encapsulate an anti-inflammatory agent, triamcinolone acetonide (TA, Scheme 5-1). Loading efficiency, stability of gels, and release kinetics in response to the presence of enzymes has been investigated.

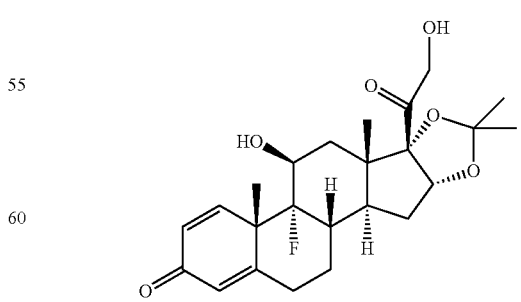

Scheme 5-1.

Chemical structure of corticosteroid based anti-inflammatory agent, triamcinolone acetonide (TA).

Morphology of Self-Assembled Gels of Triamcinolone Acetonide Encapsulated Hydrogels.

Scanning electron microscope images revealed that TA encapsulated SMS hydrogels (20% (v/v) DMSO in water) are highly porous and similar to SMS gels without TA.

Controlled Release of Triamcinolone Acetonide.

Figure 12:
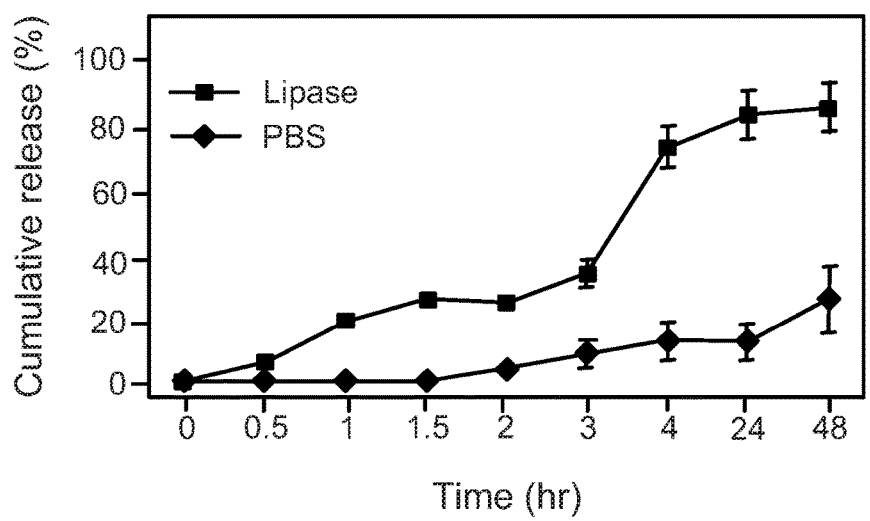
FIG. 12 is a graph showing controlled release of TA from self-assembled SMS hydrogels (6%, wt/v) in the absence and presence of esterase enzyme (10,000 units) at 37° C.

Corticosteroid TA has been encapsulated in SMS gels with higher loading efficiency. Release kinetic experiments reveal that TA encapsulated SMS gels do not exhibit burst release (FIG. 12). In the absence of enzymes, these gels were stable and showed only moderate release of TA (~20%) reaching a plateau within ~24 hr. On the contrary, in the presence of an esterase enzyme (lipase, 10,000 units), gels exhibited enzyme-responsive release of TA, which suggests that esterase enzyme can degrade the SMS gels in an on-demand manner to release the encapsulated drugs (FIG. 12).

Example 6

We have investigated the ability of Ascorbic acid palmitate (Asc-Pal, Scheme 6-1) based hydrogels to encapsulate the corticosteroid dexamethasone (Scheme 6-2). Loading efficiency, stability of gels and release kinetics in response to enzymes was been investigated.

Scheme 6-1. Chemical structure of
GRAS-based ascorbic acid palmitate (Asc-Pal).

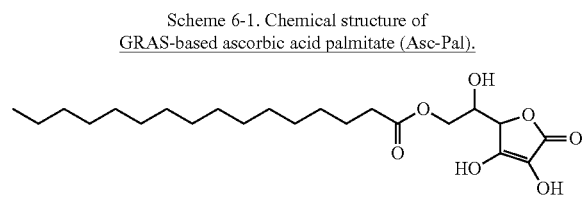

Ascorbyl palmitate (Asc-Pal)

Scheme 6-2. Chemical structure of dexamethasone.

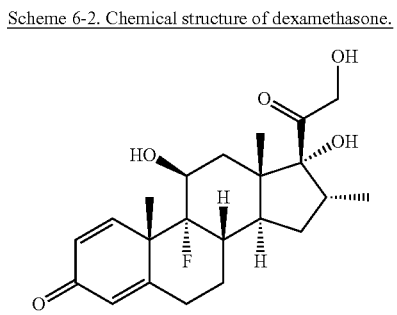

Encapsulation of Dexamethasone in GRAS-Hydrogels.

Dexamethasone is a hydrophobic drug that exhibits low water solubility. Dexamethasone encapsulated within self-assembled Asc-Pal hydrogels (20% ethanol as co-solvent) demonstrated efficient encapsulation (Table 6-1). Self-assembled fibers were isolated from dexamethasone encapsulated Asc-Pal hydrogels using multiple cycles of vortex and PBS washes. Isolated fibers were dissolved in DMSO, and the concentration of dexamethasone was measured using HPLC.

TABLE 6-1

Encapsulation of dexamethasone in Asc-Pal based hydrogels.

| Solvent | Amphiphile (Asc-Pal) concentration, % (wt/v) | Encapsulation of dexamethasone, Efficiency (%) |
|---|---|---|
| 20% Ethanol in water | 3 | 47.67% |
| 20% Ethanol in water | 6 | 62.30% |

Self-assembly of the amphiphiles is a delicate process that could be affected by additional agents. To understand the affect of dexamethasone, gelation of Asc-Pal has been explored in 20% ethanol in water by varying concentration of Asc-Pal (1-5% wt/v) while keeping concentration of dexamethasone (2 mg) constant. Results in Table 6-2 reveal that presence of dexamethasone facilitates the self-assembly of Asc-Pal and strengthen the gelation.

TABLE 6-2

Gelation of Asc-Pal at different concentrations in 20% of ethanol in water without and with (2 mg) of dexamethasone.

| Gel Percentage | Without drug | With dex (2 mg) |
|---|---|---|
| 1% | Not gel | Weak |
| 2% | weak | Gel |
| 3% | Gel | Gel |
| 4% | Gel | Gel |
| 5% | Gel | Gel |

Figure 13A:
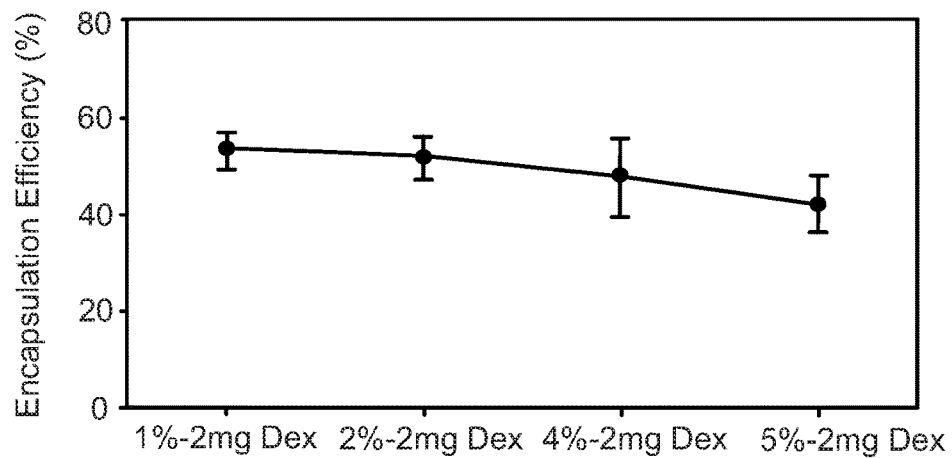
FIGS. 13A-13 B are graphs showing A) encapsulation efficiency and B) loading efficiency of Asc-Pal hydrogels (20% ethanol v/v) at different concentration of Asc-Pal amphiphile (1-5% wt/v). In all samples, 2 mg of dexamethasone was used as starting concentration for encapsulation.
Figure 13B:
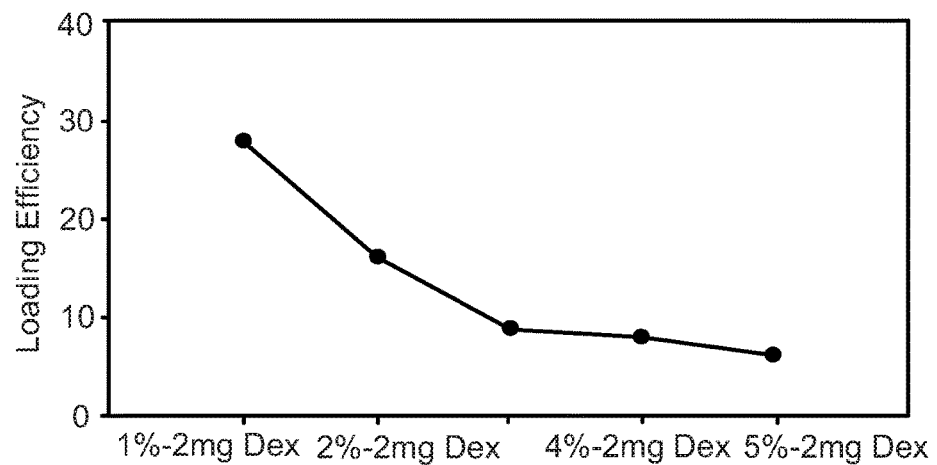

Encapsulation efficiency and loading efficiency were measured from the lyophilized fibers of Asc-Pal gels that were described in Table 6-2. FIGS. 13A-13B reveal that encapsulation and drug loading efficiencies were increased as the percentage of amphiphile decreased.

Morphology of Dexamethasone Encapsulated Self-Assembled Hydrogels.

Scanning electron microscope images revealed that dexamethasone encapsulated Asc-Pal hydrogels consist of fibrous morphology (up to micron width and several microns length) that is similar to Asc-Pal gel without dexamethasone.

On-Demand Delivery of Dexamethasone from Gras-Based Asc-Pal Self-Assembled Hydrogels.

Figure 14A:
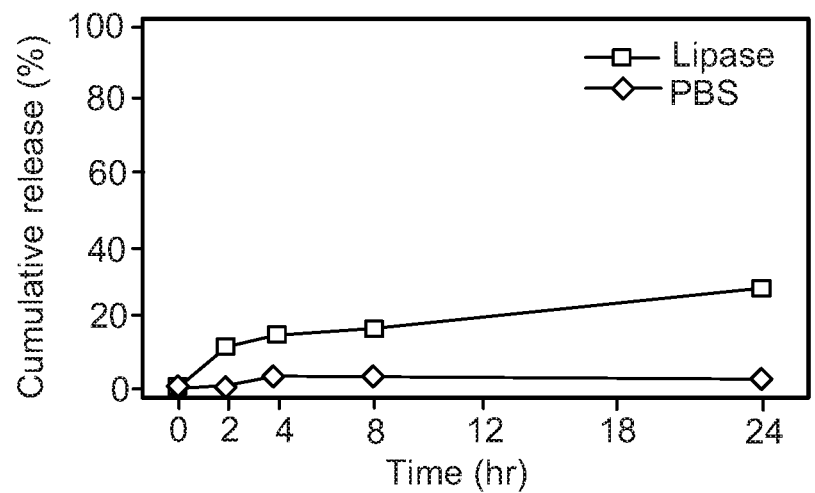
FIG. 14A-14B are graphs showing controlled release of dexamethasone from self-assembled hydrogels (ethanol:water, 1:3) of Asc-Pal (5%, wt/v) in the absence and presence of esterase enzyme (10,000 units) at 37° C. Controlled release was examined for A) 2 mg and B) 4 mg of dexamethasone encapsulated within Asc-Pal hydrogels. Similar release profile has been observed from both gels.
Figure 14B:
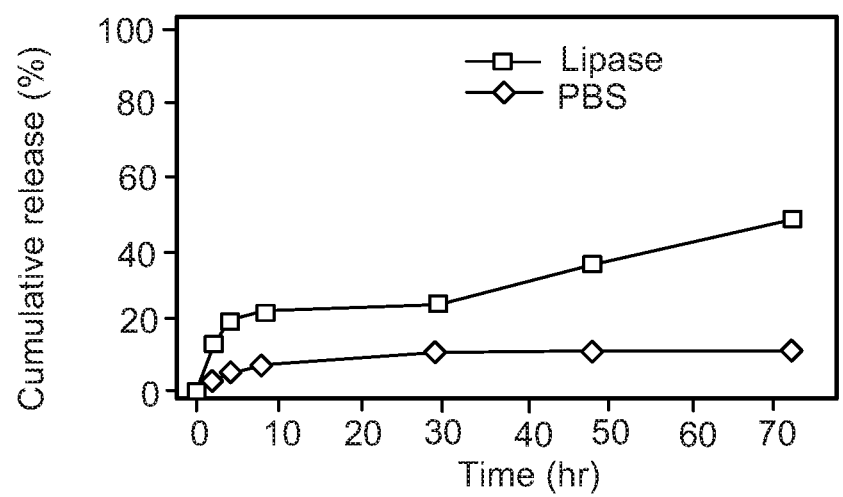

Different amounts of dexamethasone (2 and 4 mg) in 5% (wt/v) of Asc-Pal self-assembled gels (ethanol:water, 1:3) were subjected to controlled release experiments. In the absence of the esterase enzyme, dexamethasone has not been released, a moderate burst release (<10%) has been observed. On contrary, presence of lipase enzyme triggered the release of encapsulated dexamethasone. Interestingly, different starting amounts of dexamethasone gels have shown similar release profiles. FIGS. 14A-14B show the controlled release of dexamethasone from self-assembled hydrogels (ethanol:water, 1:3) of Asc-Pal (5%, wt/v) in the absence and presence of esterase enzyme (10,000 units) at 37° C. Controlled release was examined for FIG. 14A: 2 mg and FIG. 14B: 4 mg of dexamethasone encapsulated within Asc-Pal hydrogels. Similar release profile has been observed from both gels.

Figure 15A:
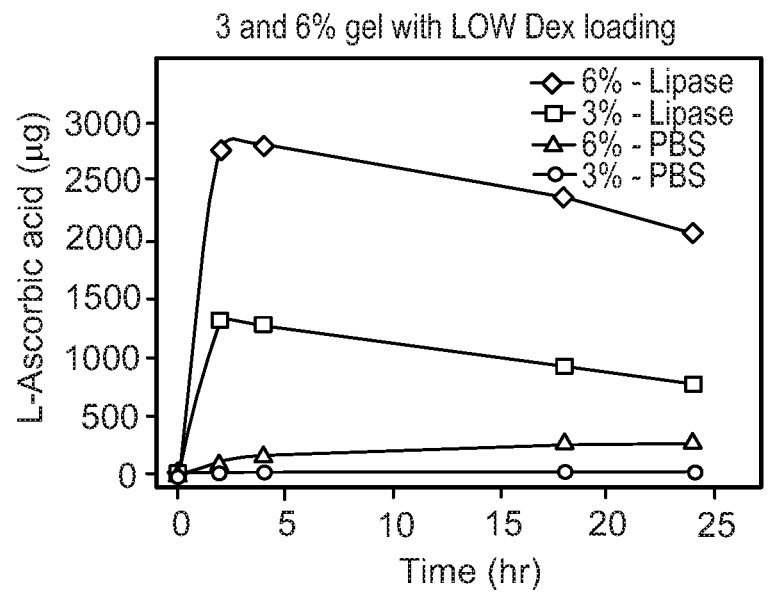
FIG. 15A-15B are graphs showing enzyme responsive degradation of Asc-Pal (3 and 6% wt/v) hydrogels to release ascorbic acid from A) low and B) high loading of dexamethasone. Release of ascorbic acid was measured with and without lipase enzyme (10,000 units) at 37° C. In the presence of enzyme, Asc-Pal was cleaved rapidly releasing ascorbic acid (within 2 hours), whereas absence of enzyme did not resulted in the presence of significant concentrations of ascorbic acid. Ascorbic acid is unstable and degrades rapidly in PBS at 37° C., thus its concentration decreases over time.
Figure 15B:
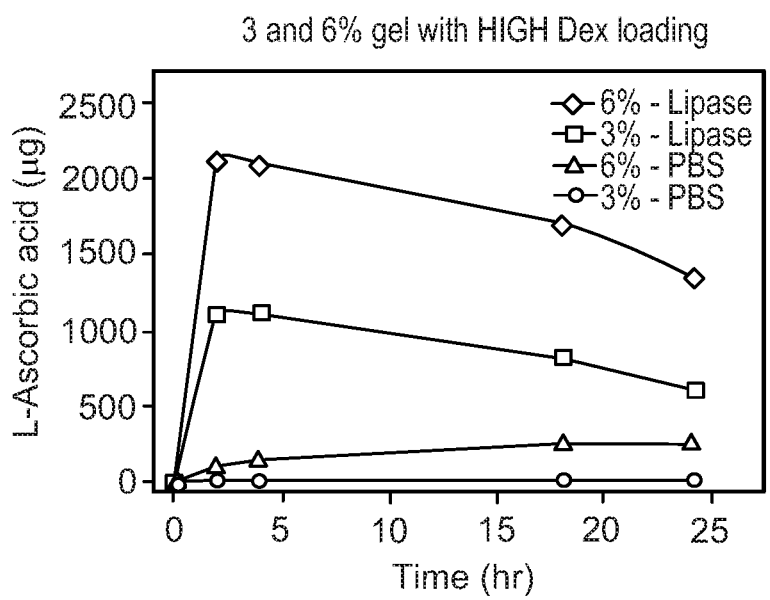

The preformed Asc-Pal hydrogel was degraded completely by the lipase (an esterase) while releasing the encapsulated dexamethasone. As enzyme responsive release of dexamethasone occurred, it is important to understand the degradation products from Asc-Pal hydrogels. Asc-Pal amphiphiles encompass an ester bond that connects ascorbic acid and palmitic acid (FIGS. 15A-15B). Thus it is anticipated that lipase degrades the hydrogel by hydrolyzing ester bonds of Asc-Pal amphiphile. The formation of byproduct ascorbic acid was followed by HPLC. To follow the formation of ascorbic acid two-sets of Asc-Pal hydrogels (3 and 6% wt/v) were made with 0.42 (FIG. 15A) and 1 (FIG. 15B) mg of dexamethasone loading. These hydrogels were subjected to lipase enzyme, enzyme responsive formation of ascorbic acid (FIGS. 15A-15B) reveal that Asc-Pal hydrogels degrade in response to the enzyme that cleavage ester bonds in the amphiphilic gelators by the hydrolase enzyme.

Figure 16:
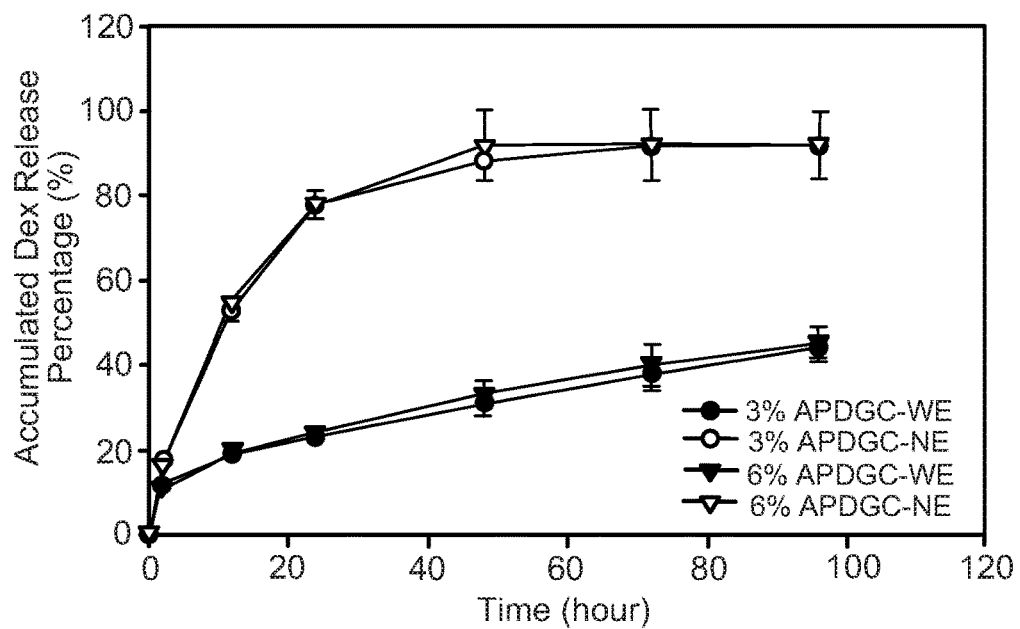
FIG. 16 is a graph showing release of dexamethasone from Asc-Pal hydrogels that were doped with an excipient glycocholic acid. 1 mg of glycocholic acid was added during the preparation of hydrogels. 3 and 6% (wt/v) of amphiphile was used to prepare gels. Release of dexamethasone was been performed in the absence (3% APDGC-NE and 6% APDCG-NE) and in the presence of (3% APDGC-WE and 6% APDCG-WE) lipase enzyme (10,000 units) at 37° C.

Addition of excipients to self-assembled hydrogels can influence the gelation ability. Strength of the hydrogels can be altered through addition of an appropriate excipient during the self-assembly process. Addition of an excipient could be used to alter the release of the encapsulated agents in addition to altering gelation strength. To modulate the gelation strength of Asc-Pal hydrogels (3 and 6%) glycocholic acid (1 mg) was added during self-assembly process, and these gels were subjected to lipase mediated degradation. Interestingly, data in FIG. 16 reveal that addition of glycocholic acid reversed the enzyme responsiveness. Presence of lipase reduced the release of dexamethasone compared to the control (PBS, FIG. 16). The rigid steroidal backbone of glycocholic acid may induce destabilization of the self-assembled lamellar structures of Asc-Pal amphiphile. Thus doping of glycocholic acid may perturb optimal encapsulation of dexamethasone that result in a non-enzymatic responsive release of dexamethasone.

Effect of Dexamethasone Structure on its Release from Asc-Pal Hydrogels.

Figure 17:
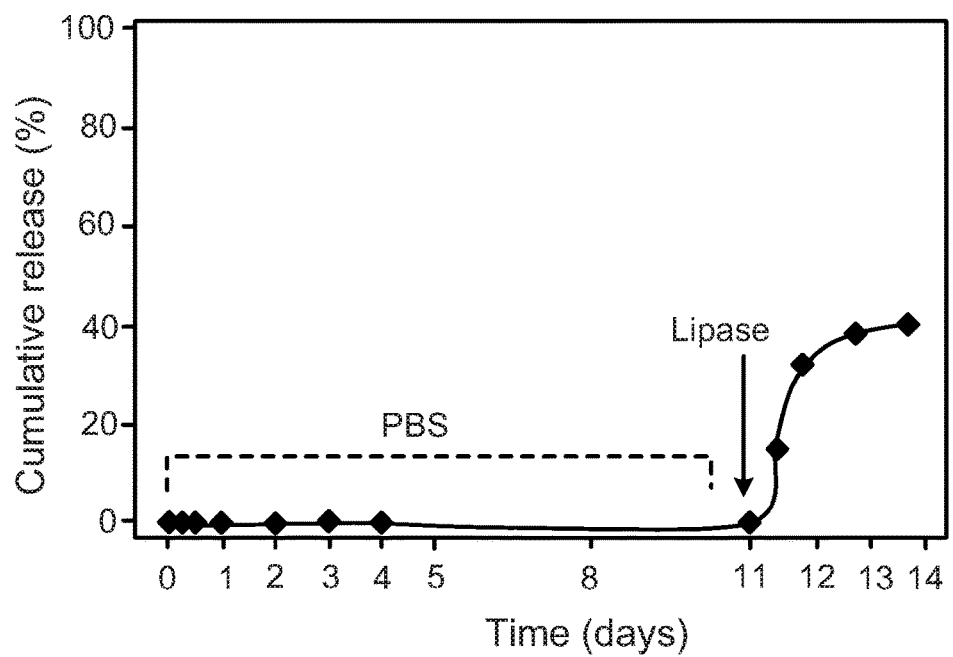
FIG. 17 is a graph showing on-demand release of dexamethasone from dexamethasone-palmitate encapsulated self-assembled hydrogels (20% (v/v) DMSO in water) of Asc-Pal (8%, wt/v) in the absence and presence of esterase enzyme (10,000 units) at 37° C. From day-0 to day-11 gels were incubated in PBS, on day-11 lipase was added (arrow) that triggered release of dexamethasone.

Hydrophobic analogue of dexamethaonse, i.e., palmitated dexamethasone (Dex-Pal) was used to incorporate Dex-Pal within self-assembled fibers of Asc-Pal. Rationale for using dexamethasone palmitate is that the presence of a hydrophobic chain facilitates efficient incorporation of hydrophobic drugs within self-assembled lamellar structures of Asc-Pal. To elucidate release kinetics, 1.6 mg of Dex-Pal has been encapsulated in 16 mg of Asc-Pal in 200 μl of 20% DMSO/water. In the absence of the esterase enzyme, upon incubation in PBS at 37° C., dexamethasone-palmitate encapsulated Asc-Pal hydrogels did not release dexamethasone (FIG. 17). Even after 11 days, there was no significant amount of dexamethasone released from these gels. However, at day 11, lipase enzyme promoted degradation of the gels to release dexamethasone in an on-demand manner (FIG. 17).

Example 7

We have investigated the ability of Ascorbic acid palmitate (Asc-Pal), gels to encapsulate the anti-inflammatory agent, Indomethacin (Scheme 7-1). Loading efficiency, stability of gels and release kinetics in response to the enzymes has been investigated. Detailed results have been summarized in following sections.

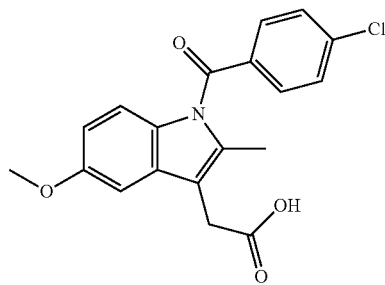 [SMILES: COc1ccc2c(c1)c(CC(=O)O)c(C)n2C(=O)c1ccc(Cl)cc1]

Scheme 7-1.

Chemical structure of non-steroidal anti-inflammatory drug (NSAID), indomethacin.

Controlled Release of Indomethacin.

Figure 18:
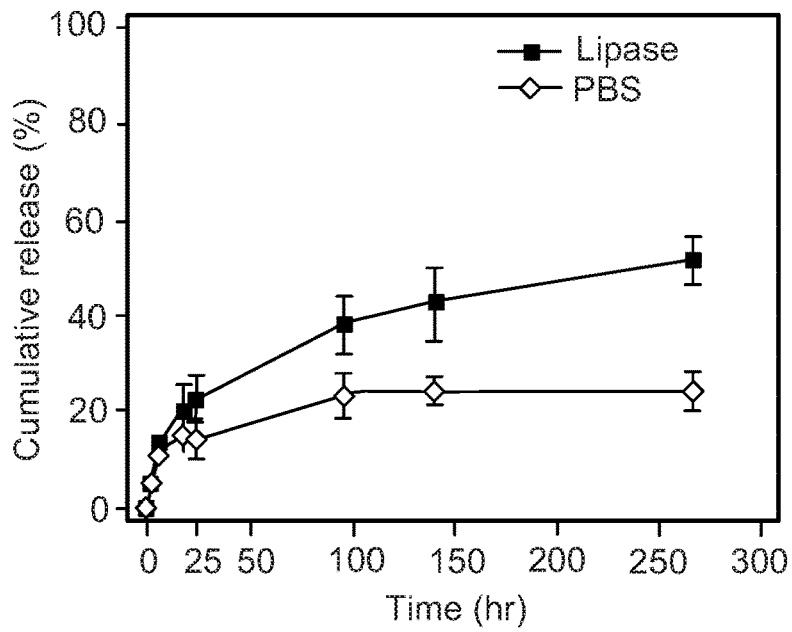
FIG. 18 is a graph showing controlled release of indomethacin from self-assembled hydrogel of Asc-Pal (6%, wt/v) in the absence and presence of esterase enzyme (10,000 units) at 37° C.

Non-steroidal anti-inflammatory drug, indomethacin has been encapsulated in Asc-Pal gels with high loading efficiency (~83%). Release kinetic experiments reveal that indomethacin encapsulated Asc-Pal gel does not exhibit burst release (FIG. 18). In the absence of enzymes, these gels were stable and showed only moderate release of indomethacin (~20%) and reached a plateau within ~24 hr. On the contrary, in the presence of an esterase enzyme (lipase, 10,000 units), the gels exhibit enzyme-responsive release of TA. This demonstrates that enzymes can degrade the SMS gels in an on-demand manner to release the encapsulated drugs (FIG. 18).

Example 8

Figure 19:
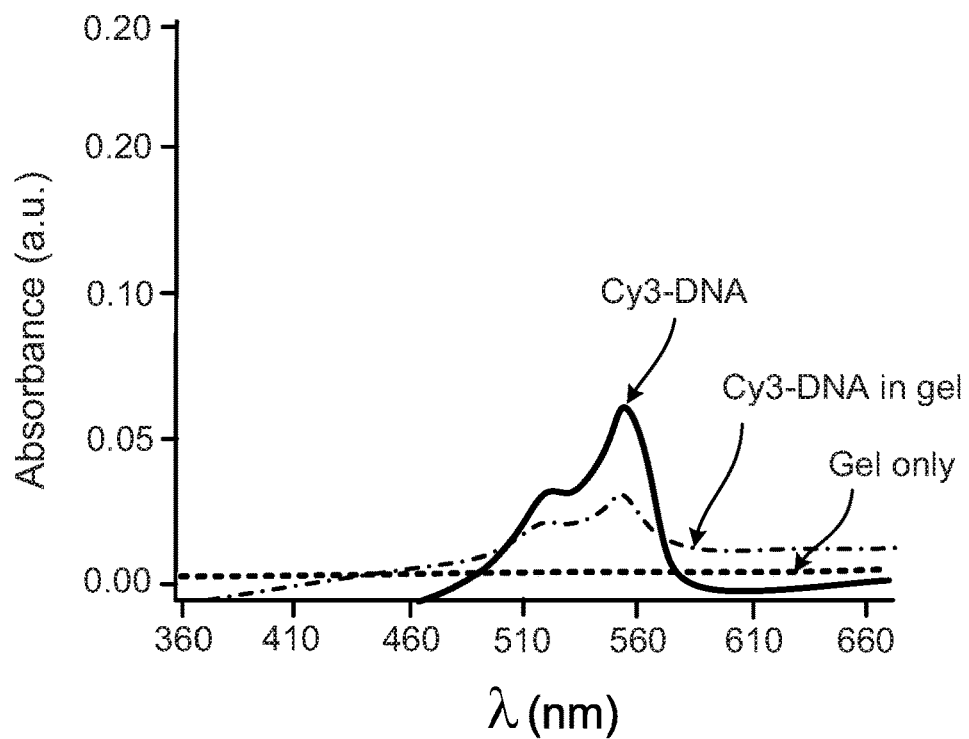
FIG. 19 is a graph showing quantification of DNA in SMS hydrogel fibers.

Self-assembled nanofibrous hydrogels of SMS amphiphiles have been used for encapsulating small interference RNA (siRNA). In this instance, GL3 siRNA (sense: 5'-CUU ACG CUG AGU ACU UCG AdTdT-3' (SEQ ID NO:1) and antisense: 5'-UCG AAG UAC UCA GCG UAA GdTdT-3' (SEQ ID NO:2)) is known to silence firefly luciferase in cells. GL3 encapsulated hydrogel has shown fibrous-like morphology. To quantify the encapsulation efficiency, fluorescent dye (Cy-3) labeled DNA with same sequence as GL3 was chosen to mimic similar charge that can influence encapsulation. After encapsulating the siRNA into SMS hydrogels, inherent gelation properties such as minimum gelation concentration and gel stability have not been perturbed by presence of siRNA. Quantification of encapsulated Cy3-DNA revealed that SMS hydrogels entrapped DNA with 15% encapsulation efficiency. However, further optimization of protocols could significantly enhance the encapsulation efficiency. DNA encapsulated self-assembled fibers were washed with phosphate buffered saline to remove non-encapsulated DNA. Subsequently, DNA encapsulated fibers were dissolved in DMSO and presence of DNA has been quantified using absorbance spectra (FIG. 19). Referring to FIG. 19, the presence of an absorption peak at 555 nm for DNA-encapsulated SMS hydrogel compared to only SMS hydrogel clearly suggests that DNA has been encapsulated within the gel.

Example 9

We have investigated the ability of GRAS-amphiphiles, Ascorbic acid palmitate (Asc-Pal, Sorbitan monostearate (SMS) and Triglycerol monostearate (TG-18, Scheme 9-1) based hydrogels to encapsulate insulin. Loading efficiency, stability of gels and morphology of the gels was been investigated.

Scheme 9-1. Structure of triglycerol monostearate (available in both forms).

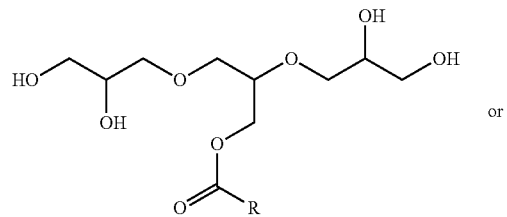

or

-continued

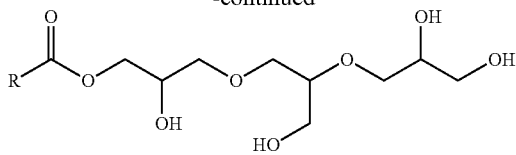

Encapsulation of Insulin in GRAS-Hydrogels.

Insulin was encapsulated within self-assembled Asc-Pal or SMS hydrogels demonstrated efficient encapsulation between 58-80%. Self-assembled particles were isolated from insulin encapsulated SMS hydrogels using multiple cycles of vortex and PBS washes. Isolated particles were dissolved, and the concentration of insulin was measured using Bradford assay. Loading efficiency of insulin in GRAS-based hydrogels was 15-35% (wt/wt).

Morphology of Insulin Encapsulated SMS Hydrogels.

Insulin encapsulated SMS hydrogels were characterized under scanning electron microscope (SEM). Hydrogels were tested as native gels, lyophilized xerogels and xerogels in the presence of stabilizers such as trehalose and Tween-20. These hydrogels showed particle-like morphology under scanning electron microcopy.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

aqueous solvents containing an organic solvent in a concentration of between 0.5 and 75 vol/vol % of the total solvent volume, wherein the gelator meets the requirements of the FDA for Generally Recognized As Safe compounds; and one or more agents for delivery from the gel composition;

wherein the self-assembled gel composition comprises nanostructures comprising lamellar structures, fibers, sheet-like structures, tape-like structures, nanoparticles, or combinations thereof, each comprising the enzyme cleavable amphiphilic gelator;

wherein the one or more agents are at least partially encapsulated or entrapped by the nano structures, and wherein the agent is released from the gel composition in the presence of enzyme, and wherein the self-assembled gel is a viscous homogenous gel stable to inversion, optionally wherein solvent is removed from the gel composition by centrifugation, washing, lyophilization, drying, or combinations thereof.

2. The self-assembled gel composition of claim 1 wherein the enzyme cleavable amphiphilic gelator is an ascorbyl alkanoate selected from the group consisting of ascorbyl palmitate, ascorbyl decanoate ascorbyl laurate, ascorbyl caprylate, ascorbyl myristate, ascorbyl oleate, and combinations thereof.

3. The self-assembled gel composition of claim 2, wherein the ascorbyl alkanoate is ascorbyl palmitate.

4. The self-assembled gel composition of claim 1, wherein the enzyme cleavable amphiphilic gelator is a sorbitan alkanoate selected from the group consisting of sorbitan monostearate, sorbitan decanoate, sorbitan laurate, sorbitan caprylate, sorbitan myristate, sorbitan oleate, and combinations thereof.

What is claimed is:

1. A self-assembled gel composition controllably releasing an agent comprising a gel composition prepared by self-assembly of a homogeneous solution of an enzyme cleavable amphiphilic gelator having a molecular weight of 2500 or less in a concentration of greater than 3 wt/vol % in one or more 5. The self-assembled gel composition of claim 4, wherein the sorbitan alkanoate is sorbitan monostearate.

6. The self-assembled gel composition of claim 1, wherein the enzyme cleavable amphiphilic gelator is a triglycerol monoalkanoate selected from the group consisting of triglycerol monopalmitate, triglycerol monodecanoate, triglycerol monolaurate, triglycerol monocaprylate, triglycerol monomyristate, triglycerol monostearate, triglycerol monooleate, and combinations thereof.

7. The self-assembled gel composition of claim 6, wherein the triglycerol monoalkanoate is triglycerol monopalmitate.

8. The self-assembled gel composition of claim 1, wherein the enzyme cleavable amphiphilic gelator is a sucrose alkanoate selected from the group consisting of sucrose palmitate, sucrose decanoate, sucrose laurate, sucrose caprylate, sucrose myristate, sucrose oleate, and combinations thereof.

9. The self-assembled gel composition of claim 8, wherein the sucrose alkanoate is sucrose palmitate.

10. The self-assembled gel composition of claim 1, wherein the enzyme cleavable amphiphilic gelator is glycocholic acid.

11. A self-assembled gel composition controllably releasing an agent comprising
   a gel composition prepared by self-assembly of a homogeneous solution containing at least 3 wt/vol % of an enzyme cleavable amphiphilic gelator having a molecular weight of 2500 or less, a non-independent gelator, in one or more aqueous solvents containing an organic solvent in a concentration of between 0.5 and 75 vol/vol % of the total solvent volume, wherein the gelator meets the requirements of the FDA for Generally Recognized As Safe compounds; and
   one or more agents for delivery from the gel composition after exposure to enzyme under physiological conditions;
   wherein the enzyme cleavable amphiphilic gelator and the non-independent gelator in one or more aqueous solvents containing an organic solvent in a concentration of between 0.5 and 75 vol/vol % of the total solvent volume co-self-assemble into a viscous homogeneous gel,
   wherein the gel composition is stable to inversion and comprises nanostructures comprising lamellar structures, fibers, sheet-like structures, tape-like structures, nanoparticles, or combinations thereof, each comprising the enzyme cleavable amphiphilic gelator and the non-independent gelator;
   wherein the one or more agents are at least partially encapsulated or entrapped by the nano structures; and
   wherein solvent is removed from the gel composition by centrifugation, washing, lyophilization, drying, or combinations thereof.

12. The self-assembled gel composition of claim 1, wherein the solvent is removed completely and the self-assembled gel composition is in the form of a powder or powder formulation.

13. The self-assembled gel composition of claim 1, from which all of the solvent has been removed.

14. The self-assembled gel composition of claim 1, wherein the organic solvent is selected from the group consisting of benzene, toluene, carbon tetrachloride, acetonitrile, glycerol, 1,4-dioxane, dimethyl sulfoxide, ethylene glycol, methanol, chloroform, hexane, acetone, N, N'-dimethyl formamide, ethanol, and combinations thereof.

15. The self-assembled gel composition of claim 1, wherein the one or more agents are selected from the group consisting of peptides, proteins, nucleic acids, polynucleotides, small molecule agents, and combinations thereof.

16. The self-assembled gel composition of claim 1, wherein the one or more agents are selected from the group consisting of anti-inflammatory agents, chemotherapeutics, PARP-inhibitors, steroids, vitamins, anti-pain agents, anti-pyretic agents, anti-depression agents, vasodilators, vasoconstrictors, immune-suppressants, tissue regeneration promoters, combinations thereof.

17. The self-assembled gel composition of claim 1, wherein the one or more agents are selected from the group consisting of dexamethasone, temozolomide, triamcinolone acetonide, camptothecin, iodomethacin, paclitaxel, carmustine, curcumin, cisplatin, BMS-536924, ethambutol, insulin, 1,10-Dioctadecyl-3,3,30,30-tetramethylindodicarbocyanine 4-chlorobenzenesulfonate salt (DiD) dye, Cy3 dye, and small interfering RNA (siRNA).

18. The self-assembled gel composition of claim 16, wherein the PARP-inhibitors are selected from the group consisting of NU1025, BSI-201, AZD-2281, ABT-888, AGO-14699, 4-hydroxyquinazoline, 3-aminobenzamide, 1,5-isoquinolinediol, 4-amino-1,8-naphthalimide, and $O^6$-benzylguanine.

19. The self-assembled gel composition of claim 1, wherein the agent is a chemotherapeutic agent.

20. The self-assembled gel composition of claim 19, wherein the chemotherapeutic agent is temozolomide, carmustine, camptothecin, or paclitaxel.

21. The self-assembled gel composition of claim 1, wherein the enzyme cleavable amphiphilic gelator having a molecular weight of 2500 or less is selected from the group consisting of ascorbyl alkanoate, sorbitan alkanoate, triglycerol monoalkanoate, sucrose alkanoate, glycocholic acid, and combinations thereof.

22. The self-assembled gel composition of claim 1, further comprising a non-independent gelator.

23. The self-assembled gel composition of claim 1, wherein the nanostructures are lamellar structures.

24. The self-assembled gel composition of claim 1 wherein the enzyme cleavable amphiphilic gelator and the one or more aqueous solvents are mixed with heating and the viscous homogeneous gel forms within 15 to 45 minutes of cooling.

25. The self-assembled gel composition of claim 1 comprising 4 wt/vol % or more of the enzyme cleavable amphiphilic gelator.

26. The self-assembled gel composition of claim 1 wherein in the absence of enzyme, the agent is released with a minimal burst of less than 20% of agent in the self-assembled gel composition measured at 37° C. in phosphate buffered saline.

27. The self-assembled gel composition of claim 1 wherein the enzyme cleavable amphiphilic gelator is dissolved in a mixture of water and the organic solvent to form a stable gel in the absence of buffer.

28. The self-assembled gel composition of claim 1 in the form of an inhalable or intranasal dried powder.

29. The self-assembled gel composition of claim 1 in the form of dry powder incorporated into a lozenge or chewing gum.

30. The self-assembled gel composition of claim 11, wherein the non-independent gelator is selected from the group consisting of alpha tocopherol acetate, retinyl acetate, and retinyl palmitate.

31. The self-assembled gel composition of claim 11 wherein, in the absence of enzyme, the agent is released with a minimal burst of less than 20% of the agent in the self-assembled gel composition measured at 37° C. in phosphate buffered saline.

32. The self-assembled gel composition of claim 1, wherein the organic solvent is in a concentration of between 0.5 and 30 vol/vol % of the solvent volume in the homogeneous solution.

33. The self-assembled gel composition of claim 11, wherein the organic solvent is in a concentration of between 0.5 and 30 vol/vol % of the solvent volume in the homogeneous solution.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: GL3 siRNA

<400> SEQUENCE: 1
cuuacgcuga guacuucgat t                                              21

<210> SEQ ID NO 2
<211> LENGTH: 21
<212> TYPE: DNA
<213> ORGANISM: Artificial Sequence
<220> FEATURE:
<223> OTHER INFORMATION: GL3 siRNA

<400> SEQUENCE: 2
ucgaaguacu cagcguaagt t                                              21
```